United States Patent
McAuley et al.

(10) Patent No.: US 10,842,964 B2
(45) Date of Patent: Nov. 24, 2020

(54) BREATHING ASSISTANCE APPARATUS

(71) Applicant: Fisher & Paykel Healthcare Limited, Auckland (NZ)

(72) Inventors: Alastair Edwin McAuley, Auckland (NZ); Craig Robert Prentice, Auckland (NZ); Oliver Gleeson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/775,154

(22) Filed: Jan. 28, 2020

(65) Prior Publication Data
US 2020/0164169 A1 May 28, 2020

Related U.S. Application Data

(63) Continuation of application No. 16/378,212, filed on Apr. 8, 2019, which is a continuation of application (Continued)

(30) Foreign Application Priority Data

Feb. 23, 2004 (NZ) .......................... 531332
Aug. 6, 2004 (NZ) .......................... 534606

(51) Int. Cl.
*A61M 16/06* (2006.01)
*A61M 16/16* (2006.01)
(Continued)

(52) U.S. Cl.
CPC .... *A61M 16/0666* (2013.01); *A61M 16/0057* (2013.01); *A61M 16/0069* (2014.02);
(Continued)

(58) Field of Classification Search
CPC .......... A61M 16/0057; A61M 16/0069; A61M 16/06; A61M 16/0611; A61M 16/0616;
(Continued)

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| AU | 2003246441 | 12/2003 |
| CA | 1311662 | 12/1992 |

(Continued)

OTHER PUBLICATIONS

U.S. Appl. No. 60/493,515, filed Aug. 8, 2002, Sleeper et al.
(Continued)

*Primary Examiner* — Annette Dixon
(74) *Attorney, Agent, or Firm* — Knobbe, Martens, Olson & Bear, LLP

(57) ABSTRACT

In one embodiment, a nasal cannula is shaped to fit within a user's nares, where the nasal cannula includes at least one prong allowing high flow delivery of humidified gases and creates positive airway pressure in the patient's airway. The prongs have angled ends such that, in use, gases flowing through the prongs are directed to the user's nasal passages. The nasal cannula body is partially swivelling and preferably has a ball joint connector. In another embodiment the nasal cannula may have at least one flared end prong that preferably seals within a patient's nare.

20 Claims, 10 Drawing Sheets

Related U.S. Application Data

No. 15/947,021, filed on Apr. 6, 2018, now Pat. No. 10,252,015, which is a continuation of application No. 14/333,134, filed on Jul. 16, 2014, now Pat. No. 9,974,914, which is a continuation of application No. 10/598,026, filed as application No. PCT/NZ2005/000023 on Feb. 18, 2005, now Pat. No. 8,783,257.

(51) Int. Cl.
*A61M 16/08* (2006.01)
*A61M 16/00* (2006.01)
*A61M 16/10* (2006.01)

(52) U.S. Cl.
CPC ...... *A61M 16/024* (2017.08); *A61M 16/0616* (2014.02); *A61M 16/0683* (2013.01); *A61M 16/08* (2013.01); *A61M 16/0816* (2013.01); *A61M 16/0825* (2014.02); *A61M 16/0875* (2013.01); *A61M 16/109* (2014.02); *A61M 16/16* (2013.01); *A61M 2205/0216* (2013.01)

(58) Field of Classification Search
CPC .......... A61M 16/0633; A61M 16/0666; A61M 16/0683; A61M 16/08; A61M 16/0816; A61M 16/0825; A61M 16/0875; A61M 16/109; A61M 16/16; A61M 16/208; A61M 2016/0661; A61M 2205/0216; A61M 2209/088; A61M 2210/0618
See application file for complete search history.

(56) References Cited

U.S. PATENT DOCUMENTS

| | | | |
|---|---|---|---|
| 577,926 A | 3/1897 | Miller | |
| 718,470 A | 1/1903 | Jones | |
| 751,091 A | 2/1904 | Moran | |
| 770,013 A | 9/1904 | Linn | |
| 1,635,545 A | 7/1927 | Drager | |
| 2,126,755 A | 8/1938 | Dreyfus | |
| 2,228,218 A | 1/1941 | Schwartz | |
| 2,241,535 A | 5/1941 | Boothby et al. | |
| 2,296,150 A | 9/1942 | Dockson et al. | |
| 2,353,643 A | 7/1944 | Bulbulian | |
| 2,359,506 A | 10/1944 | Battley et al. | |
| 2,388,604 A | 11/1945 | Eisenbud | |
| 2,452,845 A | 11/1948 | Fisher | |
| 2,508,050 A | 5/1950 | Valente | |
| 2,693,800 A | 11/1954 | Caldwell | |
| 2,738,788 A | 3/1956 | Matheson et al. | |
| 2,843,121 A | 7/1958 | Hudson | |
| 2,859,748 A | 11/1958 | Hudson | |
| 2,875,759 A | 3/1959 | Galleher | |
| 2,894,506 A * | 7/1959 | Rose .................. | A62B 9/025 128/204.28 |
| 2,939,458 A | 6/1960 | Lundquist | |
| 3,424,633 A | 1/1969 | Corrigall et al. | |
| 3,490,452 A | 1/1970 | Greenfield | |
| 3,599,635 A | 8/1971 | Kenneth | |
| 3,682,171 A | 8/1972 | Dali et al. | |
| 3,834,682 A | 9/1974 | McPhee | |
| 3,850,171 A | 11/1974 | Ball et al. | |
| 3,894,562 A | 7/1975 | Mosley et al. | |
| 3,972,321 A | 8/1976 | Proctor | |
| 3,977,432 A | 8/1976 | Vidal | |
| 3,992,720 A | 11/1976 | Nicolinas | |
| 4,090,510 A | 5/1978 | Segersten | |
| D250,047 S | 10/1978 | Lewis et al. | |
| D250,131 S | 10/1978 | Lewis et al. | |
| 4,127,130 A | 11/1978 | Naysmith | |
| 4,150,464 A | 4/1979 | Tracy | |
| D252,322 S | 7/1979 | Johnson | |
| 4,201,205 A | 5/1980 | Bartholomew | |
| 4,258,710 A | 3/1981 | Reber | |
| 4,266,540 A | 5/1981 | Panzik et al. | |
| 4,278,082 A | 7/1981 | Blackmer | |
| 4,354,488 A | 10/1982 | Bartos | |
| 4,367,735 A | 1/1983 | Dali | |
| 4,378,011 A | 3/1983 | Warncke et al. | |
| 4,437,462 A | 3/1984 | Piljay | |
| 4,454,880 A | 6/1984 | Muto et al. | |
| 4,574,799 A | 3/1986 | Warncke et al. | |
| 4,603,602 A | 8/1986 | Montesi | |
| 4,621,632 A | 11/1986 | Bartels et al. | |
| 4,644,974 A | 2/1987 | Zingg | |
| 4,676,241 A | 6/1987 | Webb et al. | |
| D293,613 S | 1/1988 | Wingler | |
| 4,753,233 A | 6/1988 | Grimes | |
| 4,782,832 A | 11/1988 | Trimble et al. | |
| 4,836,200 A | 6/1989 | Clark et al. | |
| 4,856,508 A | 8/1989 | Tayebi | |
| 4,907,584 A | 3/1990 | McGinnis | |
| 4,915,104 A | 4/1990 | Marcy | |
| 4,915,105 A | 4/1990 | Lee | |
| 4,919,128 A | 4/1990 | Kopala et al. | |
| 4,938,209 A | 7/1990 | Fry | |
| 4,941,467 A | 7/1990 | Takata | |
| 4,944,310 A | 7/1990 | Sullivan | |
| D310,431 S | 9/1990 | Bellm | |
| 4,958,658 A | 9/1990 | Zajac | |
| 4,971,051 A | 11/1990 | Toffolon | |
| 4,986,269 A | 1/1991 | Hakkinen | |
| 5,010,925 A | 4/1991 | Atkinson et al. | |
| 5,016,625 A | 5/1991 | Hsu et al. | |
| 5,031,261 A | 7/1991 | Fenner | |
| 5,042,478 A | 8/1991 | Kopala et al. | |
| D320,677 S | 10/1991 | Kumagai et al. | |
| D321,419 S | 11/1991 | Wallace | |
| 5,062,421 A | 11/1991 | Burns et al. | |
| 5,065,756 A | 11/1991 | Rapoport | |
| D322,318 S | 12/1991 | Sullivan et al. | |
| 5,074,297 A | 12/1991 | Venegas | |
| 5,094,236 A | 3/1992 | Tayebi | |
| 5,113,857 A | 5/1992 | Dickerman et al. | |
| 5,121,745 A | 6/1992 | Israel et al. | |
| 5,148,802 A | 9/1992 | Sanders et al. | |
| 5,164,652 A | 11/1992 | Johnson et al. | |
| 5,231,979 A | 8/1993 | Rose | |
| 5,243,971 A | 9/1993 | Sullivan et al. | |
| 5,245,995 A | 9/1993 | Sullivan et al. | |
| D340,317 S | 10/1993 | Cole | |
| 5,259,377 A | 11/1993 | Schroeder | |
| 5,267,556 A * | 12/1993 | Feng .................. | B63C 11/205 128/201.11 |
| 5,269,296 A | 12/1993 | Landis et al. | |
| 5,315,859 A | 5/1994 | Schommer | |
| 5,349,949 A | 9/1994 | Schegerin | |
| 5,366,805 A | 11/1994 | Fujiki et al. | |
| D354,128 S | 1/1995 | Rinehart | |
| D355,484 S | 2/1995 | Rinehart | |
| 5,400,776 A | 3/1995 | Bartholomew | |
| 5,429,683 A | 7/1995 | Le Mitouard | |
| 5,438,979 A | 8/1995 | Johnson et al. | |
| 5,441,046 A | 8/1995 | Starr et al. | |
| 5,449,206 A | 9/1995 | Lockwood | |
| 5,449,234 A | 9/1995 | Gipp et al. | |
| 5,458,202 A | 10/1995 | Fellows et al. | |
| 5,460,174 A | 10/1995 | Chang | |
| 5,477,852 A | 12/1995 | Landis et al. | |
| 5,513,634 A | 5/1996 | Jackson | |
| 5,518,802 A | 5/1996 | Colvin et al. | |
| 5,533,506 A | 7/1996 | Wood | |
| 5,542,128 A | 8/1996 | Lomas | |
| 5,551,419 A | 9/1996 | Froehlich et al. | |
| 5,558,090 A | 9/1996 | James | |
| 5,570,689 A | 11/1996 | Starr et al. | |
| 5,588,423 A | 12/1996 | Smith | |
| 5,595,174 A | 1/1997 | Gwaltney | |
| 5,601,078 A | 2/1997 | Schaller et al. | |
| D378,610 S | 3/1997 | Reischel et al. | |
| 5,649,532 A | 7/1997 | Griffiths | |
| 5,657,752 A | 8/1997 | Landis et al. | |
| 5,662,101 A | 9/1997 | Ogden et al. | |

(56) References Cited

U.S. PATENT DOCUMENTS

| | | |
|---|---|---|
| 5,664,566 A | 9/1997 | Mcdonald et al. |
| 5,687,715 A | 11/1997 | Landis |
| 5,690,097 A | 11/1997 | Howard et al. |
| 5,724,965 A | 3/1998 | Handke et al. |
| 5,752,510 A | 5/1998 | Goldstein |
| 5,755,578 A | 5/1998 | Contant et al. |
| 5,806,727 A | 9/1998 | Joseph |
| 5,807,295 A | 9/1998 | Hutcheon et al. |
| 5,746,201 A | 12/1998 | Kidd |
| 5,857,460 A | 1/1999 | Popitz |
| 5,884,624 A | 3/1999 | Barnett et al. |
| 5,904,278 A | 5/1999 | Barlow et al. |
| 5,918,598 A | 7/1999 | Belfer |
| 5,921,239 A * | 7/1999 | McCall ............... A61M 16/06 128/205.25 |
| 5,924,420 A | 7/1999 | Reischel |
| 5,941,245 A | 8/1999 | Hannah et al. |
| 5,943,473 A | 8/1999 | Levine |
| 5,953,763 A | 9/1999 | Gouget |
| 5,966,745 A | 10/1999 | Schwartz et al. |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,135,109 A | 10/2000 | Blasdell et al. |
| 6,135,432 A | 10/2000 | Hebblewhite et al. |
| 6,192,886 B1 | 2/2001 | Rudolph |
| D440,302 S | 4/2001 | Wolfe |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| D455,891 S | 4/2002 | Biedrzycki |
| 6,398,197 B1 | 6/2002 | Dickinson et al. |
| 6,412,487 B1 | 7/2002 | Gunaratnam et al. |
| 6,412,488 B1 | 7/2002 | Barnett |
| 6,418,928 B1 | 7/2002 | Bordewick et al. |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,526,978 B2 | 3/2003 | Dominguez |
| 6,530,373 B1 | 3/2003 | Patron et al. |
| 6,561,188 B1 | 5/2003 | Ellis |
| 6,561,190 B1 | 5/2003 | Kwok |
| 6,561,191 B1 | 5/2003 | Kwok |
| 6,581,594 B1 | 6/2003 | Drew et al. |
| 6,581,601 B2 | 6/2003 | Ziaee |
| 6,581,602 B2 | 6/2003 | Kwok et al. |
| 6,584,977 B1 | 7/2003 | Serowski |
| 6,588,424 B2 | 7/2003 | Bardel |
| 6,615,832 B1 | 9/2003 | Chen |
| 6,629,531 B2 | 10/2003 | Gleason et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| D485,905 S | 1/2004 | Moore |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,736,139 B1 | 5/2004 | Wix |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,997,187 B2 | 2/2006 | Wood et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,066,179 B2 | 6/2006 | Eaton et al. |
| 7,077,126 B2 | 7/2006 | Kummer et al. |
| D526,094 S | 8/2006 | Chen |
| 7,096,864 B1 | 8/2006 | Mayer et al. |
| D533,269 S | 12/2006 | McAuley et al. |
| 7,178,525 B2 | 2/2007 | Matula, Jr. et al. |
| 7,178,528 B2 | 2/2007 | Lau |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,287,528 B2 | 10/2007 | Ho et al. |
| 7,290,546 B2 | 11/2007 | Sprinkle et al. |
| 7,296,575 B1 | 11/2007 | Radney |
| 7,318,437 B2 | 1/2008 | Gunaratnam et al. |
| 7,353,827 B2 | 4/2008 | Geist |
| 7,357,136 B2 | 4/2008 | Ho et al. |
| 7,406,966 B2 | 8/2008 | Wondka et al. |
| 7,448,386 B2 | 11/2008 | Ho et al. |
| 7,487,772 B2 | 2/2009 | Ging et al. |
| 7,493,902 B2 | 2/2009 | White et al. |
| D589,139 S | 3/2009 | Guney |
| 7,523,754 B2 | 4/2009 | Lithgow et al. |
| D595,841 S | 7/2009 | McAuley et al. |
| 7,562,658 B2 | 7/2009 | Madaus et al. |
| 7,597,100 B2 | 10/2009 | Ging |
| 7,640,934 B2 | 1/2010 | Zollinger et al. |
| 7,658,189 B2 | 2/2010 | Davidson et al. |
| 7,665,464 B2 | 2/2010 | Kopacko et al. |
| D612,933 S | 3/2010 | Prentice |
| 7,681,575 B2 | 3/2010 | Wixey et al. |
| 7,694,677 B2 | 4/2010 | Tang |
| 7,703,457 B2 | 4/2010 | Barnett et al. |
| 7,753,051 B2 | 7/2010 | Burrow et al. |
| D623,288 S | 9/2010 | Lubke |
| 7,814,911 B2 | 10/2010 | Bordewick et al. |
| 7,827,990 B1 | 11/2010 | Melidis et al. |
| 7,856,982 B2 | 12/2010 | Matula et al. |
| 7,877,817 B1 | 2/2011 | Ho |
| 7,896,003 B2 | 3/2011 | Matula et al. |
| 7,931,024 B2 | 4/2011 | Ho et al. |
| 7,934,501 B2 | 5/2011 | Fu |
| 7,942,150 B2 | 5/2011 | Guney et al. |
| 7,992,560 B2 | 8/2011 | Burton et al. |
| 8,042,539 B2 | 10/2011 | Chandran et al. |
| 8,042,541 B2 | 10/2011 | Amarasinghe et al. |
| 8,109,271 B2 | 2/2012 | Vandine et al. |
| 8,136,524 B2 | 3/2012 | Ging et al. |
| 8,136,525 B2 | 3/2012 | Lubke et al. |
| 8,171,933 B2 | 5/2012 | Xue et al. |
| D661,796 S | 6/2012 | Andrews et al. |

(56) References Cited

U.S. PATENT DOCUMENTS

| | | |
|---|---|---|
| 8,245,711 B2 | 8/2012 | Matula et al. |
| 8,371,302 B2 | 2/2013 | Ging et al. |
| 8,397,727 B2 | 3/2013 | Ng et al. |
| 8,443,807 B2 | 5/2013 | McAuley et al. |
| D686,313 S | 7/2013 | Matula et al. |
| 8,479,726 B2 | 7/2013 | McAuley |
| 8,479,741 B2 | 7/2013 | McAuley et al. |
| 8,567,404 B2 | 10/2013 | Davidson et al. |
| 8,631,793 B2 | 1/2014 | Omura et al. |
| 8,631,799 B2 | 1/2014 | Davenport |
| 8,636,005 B2 | 1/2014 | Gradon et al. |
| 8,701,667 B1 | 4/2014 | Ho et al. |
| 8,714,157 B2 | 5/2014 | McAuley et al. |
| 8,720,444 B2 | 5/2014 | Chang |
| 8,757,157 B2 | 6/2014 | Price et al. |
| 8,783,257 B2 | 7/2014 | McAuley et al. |
| 8,869,797 B2 | 10/2014 | Davidson et al. |
| 8,869,798 B2 | 10/2014 | Wells et al. |
| 8,875,709 B2 | 11/2014 | Davidson et al. |
| 8,944,061 B2 | 2/2015 | D'Souza et al. |
| 8,950,404 B2 | 2/2015 | Formica et al. |
| 8,960,196 B2 | 2/2015 | Henry |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,072,852 B2 | 7/2015 | McAuley et al. |
| 9,095,673 B2 | 8/2015 | Barlow et al. |
| 9,119,929 B2 | 9/2015 | McAuley et al. |
| 9,119,931 B2 | 9/2015 | D'Souza et al. |
| 9,138,555 B2 | 9/2015 | McAuley et al. |
| 9,149,596 B2 | 10/2015 | Valcic et al. |
| 9,186,474 B1 | 11/2015 | Rollins |
| 9,242,062 B2 | 1/2016 | Melidis et al. |
| 9,292,799 B2 | 3/2016 | McAuley et al. |
| 9,295,799 B2 | 3/2016 | McAuley et al. |
| 9,302,065 B2 | 4/2016 | Smith et al. |
| 9,320,566 B1 | 4/2016 | Alston, Jr. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,339,624 B2 | 5/2016 | McAuley |
| 9,375,545 B2 | 6/2016 | Darkin et al. |
| 9,381,316 B2 | 7/2016 | Ng et al. |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 | 2/2017 | McAuley et al. |
| 9,561,339 B2 | 2/2017 | McAuley et al. |
| 9,744,385 B2 | 8/2017 | Henry et al. |
| 9,884,160 B2 | 2/2018 | McAuley et al. |
| 9,901,699 B2 | 2/2018 | Veliss et al. |
| 9,901,700 B2 | 2/2018 | McAuley et al. |
| 9,907,925 B2 | 3/2018 | McAuley et al. |
| 9,974,914 B2 | 5/2018 | McAuley |
| 10,080,856 B2 | 9/2018 | McLaren et al. |
| 10,137,271 B2 | 11/2018 | McAuley et al. |
| 10,201,678 B2 | 2/2019 | Guney et al. |
| 10,252,015 B2 | 4/2019 | McAuley et al. |
| 10,258,757 B2 | 4/2019 | Allan et al. |
| 10,272,218 B2 | 4/2019 | McAuley et al. |
| 10,328,226 B2 | 6/2019 | Allan et al. |
| 10,363,387 B2 | 7/2019 | Allan et al. |
| 10,384,029 B2 | 8/2019 | McAuley et al. |
| 10,413,694 B2 | 9/2019 | Allan et al. |
| 10,463,825 B2 | 11/2019 | McAuley et al. |
| 2001/0017134 A1 | 8/2001 | Bahr |
| 2001/0020474 A1 | 9/2001 | Hecker et al. |
| 2001/0029952 A1 | 10/2001 | Curran |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0039867 A1 | 4/2002 | Curro et al. |
| 2002/0046755 A1 | 4/2002 | Voss |
| 2002/0053347 A1 | 5/2002 | Ziaee |
| 2002/0059935 A1 | 5/2002 | Wood |
| 2002/0069467 A1 | 6/2002 | Immediato et al. |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0075180 A1 | 4/2003 | Raje |
| 2003/0075182 A1 | 4/2003 | Heidmann et al. |
| 2003/0079749 A1 | 5/2003 | Strickland et al. |
| 2003/0084996 A1 | 5/2003 | Alberg et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0011087 A1 | 1/2004 | Rebouillat et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118406 A1 | 6/2004 | Lithgow |
| 2004/0118412 A1 | 6/2004 | Piletti-Reyes |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2005/0011521 A1 | 1/2005 | Sprinkle et al. |
| 2005/0011524 A1 | 1/2005 | Thomlinson et al. |
| 2005/0016532 A1 | 1/2005 | Farrell |
| 2005/0028822 A1 | 2/2005 | Sleeper et al. |
| 2005/0033247 A1 | 2/2005 | Thompson |
| 2005/0045182 A1 | 3/2005 | Wood et al. |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0172969 A1 | 8/2005 | Ging |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0032504 A1 | 2/2006 | Burton et al. |
| 2006/0042629 A1 | 3/2006 | Geist |
| 2006/0042632 A1 | 3/2006 | Bishop et al. |

(56) References Cited

U.S. PATENT DOCUMENTS

| | | |
|---|---|---|
| 2006/0054169 A1 | 3/2006 | Han et al. |
| 2006/0060200 A1 | 3/2006 | Ho et al. |
| 2006/0076019 A1 | 4/2006 | Ho |
| 2006/0081256 A1 | 4/2006 | Palmer |
| 2006/0096598 A1 | 5/2006 | Ho et al. |
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0196511 A1 | 9/2006 | Lau et al. |
| 2006/0201514 A1 | 9/2006 | Jones et al. |
| 2006/0207599 A1 | 9/2006 | Busch |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283458 A1 | 12/2006 | Woodard |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0083412 A1 | 4/2008 | Henry et al. |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0142019 A1 | 6/2008 | Lewis |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0236586 A1 | 10/2008 | Mcdonald et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0014007 A1 | 1/2009 | Brambilla et al. |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0183734 A1 | 7/2009 | Kwok et al. |
| 2009/0183739 A1 | 7/2009 | Wondka |
| 2009/0223519 A1 | 9/2009 | Eifler et al. |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0051031 A1 | 3/2010 | Lustenberger et al. |
| 2010/0051034 A1 | 3/2010 | Howard |
| 2010/0083969 A1 | 4/2010 | Crumblin |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0067704 A1 | 3/2011 | Kooij |
| 2011/0072553 A1 | 3/2011 | Ho |
| 2011/0088699 A1 | 4/2011 | Skipper |
| 2011/0126838 A1 | 6/2011 | Alberici |
| 2011/0146685 A1 | 6/2011 | Allan et al. |
| 2011/0232649 A1 | 9/2011 | Collazo et al. |
| 2011/0265796 A1 | 11/2011 | Amarasinghe et al. |
| 2011/0290253 A1 | 12/2011 | McAuley |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318265 A1 | 12/2012 | Amirav et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0261432 A1 | 9/2014 | Eves et al. |
| 2014/0311492 A1 | 10/2014 | Stuebiger et al. |
| 2014/0338672 A1 | 11/2014 | D'Souza et al. |
| 2015/0033457 A1 | 2/2015 | Tryner et al. |
| 2015/0090266 A1 | 4/2015 | Melidis et al. |
| 2015/0246198 A1 | 9/2015 | Bearne et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0038707 A1 | 2/2016 | Allan et al. |
| 2016/0051786 A1 | 2/2016 | McAuley et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2017/0143925 A1 | 5/2017 | McAuley et al. |
| 2017/0239438 A1 | 8/2017 | McAuley et al. |
| 2017/0246411 A1 | 8/2017 | Mashal et al. |
| 2017/0304574 A1 | 10/2017 | McAuley et al. |

(56) References Cited

U.S. PATENT DOCUMENTS

| | | |
|---|---|---|
| 2017/0368288 A1 | 12/2017 | Stephens et al. |
| 2018/0250483 A1 | 9/2018 | Olsen et al. |
| 2018/0256844 A1 | 9/2018 | Galgali et al. |
| 2019/0001095 A1 | 1/2019 | Rose et al. |
| 2019/0030273 A1 | 1/2019 | McAuley et al. |
| 2019/0232010 A1 | 8/2019 | McAuley et al. |
| 2020/0016357 A1 | 1/2020 | McAuley et al. |
| 2020/0046928 A1 | 3/2020 | Allan |
| 2020/0108219 A1 | 4/2020 | McAuley et al. |
| 2020/0171260 A1 | 6/2020 | McLaren |
| 2020/0197644 A1 | 6/2020 | McAuley et al. |

FOREIGN PATENT DOCUMENTS

| | | |
|---|---|---|
| CA | 2648690 | 11/2007 |
| CD | 000966064-000 | 9/2008 |
| CD | 000966064-0001 | 9/2008 |
| CD | 000966064-0002 | 9/2008 |
| CD | 000966064-0003 | 9/2008 |
| CD | 000966064-0004 | 9/2008 |
| CN | 2172538 | 7/1994 |
| CN | 1780265 | 12/2005 |
| CN | 1751149 | 3/2006 |
| CN | 1784250 | 6/2006 |
| CN | 1901961 | 1/2007 |
| CN | 1905917 | 1/2007 |
| CN | 101115521 | 1/2008 |
| CN | 100502972 | 6/2009 |
| CN | 101516300 | 8/2009 |
| CN | 101541380 | 9/2009 |
| CN | 101991897 | 3/2011 |
| DE | 895692 | 11/1953 |
| DE | 29723101 U1 | 7/1998 |
| DE | 19603949 | 11/1998 |
| DE | 10312881 | 5/2004 |
| DE | 102006011151 | 9/2007 |
| EP | 0 350 322 | 1/1990 |
| EP | 0 427 474 | 5/1991 |
| EP | 0 462 701 | 12/1991 |
| EP | 0 747 078 | 12/1996 |
| EP | 1 099 452 | 5/2001 |
| EP | 0 830 180 | 3/2002 |
| EP | 1 258 266 | 11/2002 |
| EP | 1 488 820 | 12/2004 |
| EP | 1 582 231 | 10/2005 |
| EP | 2 042 209 | 4/2009 |
| EP | 2 130 563 | 12/2009 |
| EP | 2 145 645 | 1/2010 |
| EP | 1 753 495 | 9/2010 |
| EP | 1 481 702 | 9/2012 |
| EP | 2 749 176 | 7/2014 |
| EP | 1 646 910 | 8/2015 |
| EP | 2 022 528 | 3/2016 |
| EP | 2 451 518 | 10/2017 |
| FR | 2658725 | 8/1991 |
| FR | 2749176 | 12/1997 |
| GB | 190224431 | 12/1902 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2186801 | 8/1987 |
| JP | 62-024721 | 2/1987 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| WO | WO 82/003548 | 10/1982 |
| WO | WO 97/32494 | 9/1997 |
| WO | WO 98/04310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/74509 | 12/2000 |
| WO | WO 00/074758 | 12/2000 |
| WO | WO 00/078384 | 12/2000 |
| WO | WO 01/00266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/94721 | 12/2001 |
| WO | WO 01/097892 | 12/2001 |
| WO | WO 01/97892 | 12/2001 |
| WO | WO 01/097893 | 12/2001 |
| WO | WO 02/005883 | 1/2002 |
| WO | WO 02/011804 | 2/2002 |
| WO | WO 02/047749 | 6/2002 |
| WO | WO 02/074372 | 9/2002 |
| WO | WO 03/035156 | 5/2003 |
| WO | WO 03/092755 | 11/2003 |
| WO | WO 04/007010 | 1/2004 |
| WO | WO 04/096332 | 1/2004 |
| WO | WO 04/012803 | 2/2004 |
| WO | WO 04/022147 | 3/2004 |
| WO | WO 04/030736 | 4/2004 |
| WO | WO 04/041341 | 5/2004 |
| WO | WO 04/041342 | 5/2004 |
| WO | WO 04/071565 | 8/2004 |
| WO | WO 04/073777 | 9/2004 |
| WO | WO 04/073778 | 9/2004 |
| WO | WO 05/010608 | 2/2005 |
| WO | WO 05/016403 | 2/2005 |
| WO | WO 05/018523 | 3/2005 |
| WO | WO 05/021075 | 3/2005 |
| WO | WO 05/051468 | 6/2005 |
| WO | WO 05/063326 | 7/2005 |
| WO | WO 05/063328 | 7/2005 |
| WO | WO 05/079726 | 9/2005 |
| WO | WO 05/086943 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/053878 | 5/2007 |
| WO | WO 07/114492 | 10/2007 |
| WO | WO 07/147088 | 12/2007 |
| WO | WO 08/007985 | 1/2008 |
| WO | WO 08/011682 | 1/2008 |
| WO | WO 08/014543 | 2/2008 |

(56) References Cited

FOREIGN PATENT DOCUMENTS

| | | |
|---|---|---|
| WO | WO 08/030831 | 3/2008 |
| WO | WO 08/060295 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

U.S. Appl. No. 60/496,059, filed Aug. 18, 2003, Ho et al.
U.S. Appl. No. 60/529,696, filed Dec. 16, 2003, Lithgow et al.
U.S. Appl. No. 61/064,406, filed Mar. 4, 2008, Wehbeh.
U.S. Appl. No. 61/071,893, filed May 22, 2008, Wehbeh et al.
U.S. Appl. No. 61/136,617, filed Sep. 19, 2008, Wehbeh et al.
Resmed Mirage Swift™ II Nasal Pillows System product page(http://www.resmed.com/en-us/products/masks/mirage_swift_II_nasal_pillows._system/Mirage-Swift-II-Nasal-Pillows-System.html?menu=products): archived Jul. 21, 2008, 2 pp.
Resmed Mirage Swift™ II user brochure (http://www.resmed.com/en us/products/masks/mirage-swift_II_nasal_pillows_system/documents/mirage-swift-ii-np-brochure-patient-english-usa.pdf) copyright 2007, 4 pp.
ResMed Mirage Swift II Fitting (http://www;resmed.com/en-us/products/masks/mirage_swift_II_nasal_pillows_system/documents/mirage-swift_ii_np-fitting_English.pdf) copyright 2006, 2 pp.
ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.
ResMed Mirage Swift II user guide (http://www.resmed.com/en-us/products/service_and_support/documents/60893rl_mirage_swiftII_nasal_userglide_us_multi.pdf) copyright 2006, 1 p.
ResMed Mirage Swift II component card (http://www.resmed.com/en- us/products/masks/mirage_swift_II_nasal_pillows_system/documents/mirage-swift-ii-np-cc-usa.pdf); copyright 2006, 2 pp.
Resmed Swift™ LT Nasal Pillows System, product page, (http://www.resmed.com/en-us/products/masks/mirage_swift_II_nasal_pillows_system/Mirage-Swift-II-Nasal-Pillows-System.html?menu=products), Jul. 3, 2008, 2 pp.
Resmed Swift LT user brochure, (http://www.resmed.com/en-us/products/masks/mirage_swift_II_nasal_pillows_system/documents/mirage-swift-ii-np-brochure-patient-english-usa.pdf), copyright 2008, 4 pp.
Resmed Swift™ LT component card (http://www.resmed.com/en-us/assets/documents/product/swift_It/components_card/1012463_swift-It_components-card_usa_eng.pdf) copyright 2008, 46 pp.
Resmed Swift™ LT fitting guide, (http://www.resmed.com/en-us/assets/documents/product/swift-II/clinical_fact_sheet/1012406 swift-ii_fact-sheet_usa_eng.pdf), 2008, 2 pp.
Resmed Swift™ LT fact sheet (http://www.resmcd.com/en-us/assets/documents/product/swift-It/clinical_fact_sheet/1012406 swiftIt_fact-sheet_usa_eng.pdf, copyright 2008, 4 pp.
Resmed Swift™ LT image gallery (http://www.resmed.com/en-us/products/masks/swift_It_nasal_pillows_system/imagegallery.html?menu=products, Apr. 25, 2008, 2 pp.
Resmed Swift™ LT interactive fitting guide—screenshot from troubleshooting part (http://www.resmed.com/enus/assets/multimedia/product/swift-It/flash/swift-It-fitting-eng.swf), Jul. 3, 2008, 2 pp.
Puritan Bennett Breeze® SleepGear® CPAP Interface, product page (http:/puritanbennett.com/prod/product.aspx?id=233); archived Oct. 19, 2007, 2 pp.
Puritan Bennett Breeze® SleepGear® User's Guide (http://puritanbennett.com/_catalog/pdf/dfu/107598a00[I].pdf); copyright 2007, 18 pp.
Puritan Bennett Breeze® SleepGear® sales sheet (http://www.puritanbennett.com/_Catalog/PDF/Product/BreezeSleepGear.pdf) copyright 2016, 7 PP.
Puritan Bennett mask coding matrix (http://www.puritanbennett.com/_Catalog/PDF/Product/BreezeSlpGear(ST03700).pdf) copyright 2006, 3 pp.
Puritan Bennett Breeze fitting guide (http://www.puritanbennett.com/_Catalog/PDF/Product/BreezeFittingPoster.pdf, Oct. 19, 2007, 1 p.
Respironics Optilife Pillows mask product page (http://optilife.respironics.com:80/); archived Nov. 21, 2007, 2 pp.
Respironics Optilife Pillows mask part numbers page (http://optilife.respironics.com:80/Parts.aspx); archived Nov. 23, 2007, 4 pp.
Respironics Optilife Pillows mask FAQ (http;//optilife.respironics.com:80/faqs.aspx); archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask fitting guide screen shot (http://optilife.respironics.com:80/fittingGuide.aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp.
Puritan Bennett Breeze description; copyright 2000 by Mallinckrodt Inc., 4 pp.
Fisher & Paykel Opus product page, archived Sep. 3, 2009, 2 pp.
Fisher & Paykel Opus patient interface product photographs, Jul. 2007, 6 pp.
Photographs of Opus 360 nasal pillows mask patient instructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2 pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Fisher & Paykel HC200 Series Nasal CPAP Blower & Heated Humidifier User Manual, 17 pp., May 1998.
Fisher & Paykel Healthcare, FlexiFit™ 431 Full Face Mask instructions, 2010, 4 pp.
Fisher & Paykel Healthcare, FlexiFit™ 431 Full Face Mask, specification sheet, 2004, 2 pp.
Fisher & Paykel Healthcare, Interface Solutions Product Profile, 2006, 12 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464-7893), 4 pp.
Malloy, 1994, Plastic Part Design for Injection Molding, Hanswer Gardner Publications, Inc, Cincinnati, OH, 14 pp.

(56) References Cited

OTHER PUBLICATIONS

Merriam-Webster's Collegiate Dictionary, Eleventh Edition, 2004, pp. 703, 905, 1074, 1184.
Philips Respironics System One Heated Humidifier—User Manual, 2011, pp. 1-16, [retrieved on Nov. 25, 2013] from the internet: URL: http://www.cpapxchange.com/cpap-machines-biap-machines/system-one-60-seri-es-cpap-humidifier-manual.pdf front cover, pp. 3-4 and 6.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Jun. 29, 1997, Mask Frames (Source: Wayback Machine Internet Archive); http://web.archive.org/web/19970629053430/http://www.resmed.com-/maskframes/mask.htm, 2 pp/.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.--wedding.sub.--band- s.sub.--metal/48214W.html), 3 pp.
Australian Examination Report No. 1, in patent application No. AU 2013300237, dated Jun. 8, 2017, in 4 pages.
Australian Examination Report in patent application No. 2016238904 dated May 4, 2018, 5 pages.
Australian Examination Report in patent application No. 2012265597 dated Dec. 19, 2013, 5 pages.
Australian Examination Report in patent application No. 2015201920, dated Jul. 20, 2015, 3 pages.
Australian Examination Report in patent application No. 2007273324, dated May 22, 2012, 3 pages.
Australian Examination Report in patent application No. 2010241390, dated Jan. 9, 2015, 4 pages.
Australian Examination Report in patent application No. 2010241390, dated Sep. 28, 2016, 4 pages.
Australian Examination Report in patent application No. 2010246985, dated Mar. 4, 2014, 5 pages.
Australian Examination Report in patent application No. 2015202814, dated Aug. 14, 2015, 8 pages.
Australian Examination Report in patent application No. 2016202799, dated May 31, 2016, 2 pages.
Australian examination report in patent application No. 2016202801, dated Jun. 20, 2016, 2 pages.
Australian Examination Report in patent application No. 2016204384, dated Aug. 5, 2016, 2 pages.
Australian examination report in patent application No. 2017200991, dated Oct. 13, 2017, 3 pages.
Australian examination report in patent application No. 2017201021, dated Apr. 7, 2017, 6 pages.
Australian examination report in patent application No. 2018202409, dated Jan. 21, 2019, 4 pages.
Australian examination report in patent application No. 2018201975, dated Mar. 30, 2019, 4 pages.
Australian examination report in patent application No. 2018217307, dated Mar. 4, 2019, 4 pages.
Australian examination report in patent application No. 2018236891, dated Jun. 25, 2019, 3 pages.
Brazilian office action dated Jul. 11, 2019 in patent application No. BR11201211420-4.
Canadian Examination Report in patent application No. 2655839, dated Oct. 4, 2013, 2 pages.
Canadian Examination Report in patent application No. 2780310, dated Jul. 26, 2016, 4 pages.
Canadian Examination Report in patent application No. 2780310, dated Jan. 25, 2018 4 pages.
Canadian Examination Report in patent application No. 2780310, dated Oct. 9, 2018, 3 pp.
Canadian Examination Report in patent application No. 2890556, dated Jan. 27, 2016, 3 pages.
Canadian Examination Report in patent application No. 2890556, dated Nov. 28, 2016, 4 pages.
Canadian Examination Report in patent application No. 2918167, dated Oct. 3, 2016, 4 pages.
Canadian Examination Report in patent application No. 2998247, dated Jan. 8, 2019, 4 pages.
Canadian Examination Report in patent application No. 3010066, dated May 3, 2019, 4 pages.
Canadian Examination Report in patent application No. 2880749, dated May 16, 2019, 5 pages.
Canadian Examination Report in patent application No. 3017161, dated Aug. 21, 2019, 3 pp.
Chinese Examination Report in patent application No. 2007800266164, dated Feb. 17, 2011, 5 pages.
Chinese Examination Report in patent application No. 201080028029.0, dated Mar. 27, 2014, 16 pages.
Chinese Second Office Action in patent application No. 201080028029.0, dated Jan. 19, 2015, 16 pages.
Chinese Examination Report in patent application No. 201080028029.0, dated Sep. 14, 2015, 3 pages.
Chinese Examination Report in patent application No. 201080061122.1, dated Jul. 17, 2015, 10 pages.
Chinese Examination Report in patent application No. 201080061122.1, dated Sep. 3, 2015, 10 pages.
Chinese First Office Action in patent application No. 201210080441.8, dated Mar. 24, 2014, 4 pages.
Chinese Second Office Action for Chinese Patent Application No. 201210080441.8 dated Dec. 1, 2014 in 11 pages (with English translation).
Chinese Office Action in patent application No. 201610116121.1, dated Sep. 28, 2017, 5 pages.
Chinese Third Office Action in patent application No. 201610116121.1, dated Apr. 28, 2019, 16 pages.
Chinese Third Office Action in patent application No. 201080061122.1, dated Apr. 1, 2016, 5 pages.
Chinese Examination Report in patent application No. 201610114706.X, dated Jul. 30, 2018, 9 pp., with translation.
Chinese Second Examination Report in patent application No. 201610114706.X, dated Apr. 24, 2019 8 pp., with translation.
Chinese Examination Report dated Feb. 22, 2019 in patent application No. 201611251618.0.
European Extended Search Report; dated Apr. 2, 2014; Application No. 09819444.2; 8 pages.
European Examination Report in patent application No. 07808683.2, dated Jul. 8, 2015, 8 pages.
European Examination Report in patent application No. 07808683.2, dated May 9, 2018, 3 pages.
European Summons to Attend Oral Proceedings and Written Opinion dated Dec. 13, 2017 in patent application No. 09746823.5; 7 pages.
European Examination Report in patent application No. 09746823.5, dated Apr. 3, 2017, 2 pages.
European Extended Search Report in patent application No. 10774623.2, dated Sep. 8, 2015, 7 pages.
European Extended Search Report in patent application No. 10830251.4, dated Sep. 4, 2015, 7 pages.
European Examination Report, European Application 13828380.9, dated Apr. 7, 2017, 7 pp.
European Examination Report, European Application 13828380.9, dated Jul. 27, 2018, 8 pp.
European extended search report dated Jul. 23, 2018 in patent application No. 18163847.9, 7 pp.

(56) References Cited

OTHER PUBLICATIONS

European extended search report dated Sep. 21, 2018 in patent application No. 18178220.2, 7 pp.
European extended search report dated Oct. 31, 2018 in patent application No. 18171619.2, 9 pp.
European Extended Search Report in patent application No. 17179765.7, dated Dec. 11, 2017.
European Extended Search Report dated Feb. 14, 2019 in patent application No. 18195537.8.
European Search Report in patent application No. 11830981.4, dated Aug. 24, 2015, 6 pages.
Great Britain Combined Search and Examination Report in patent application No. GB1406401.8, dated May 7, 2014, 4 pages.
Great Britain Combined Search and Examination Report in patent application No. GB1406402.6, dated May 7, 2014, 6 pages.
Great Britain Examination Report in patent application No. GB1119385.1, dated May 9, 2013, 4 pages.
Great Britain Search and Examination Report, in patent application No. GB1210075.6, dated Mar. 14, 2013, 2 pages.
Great Britain Combined Search and Examination Report in patent application No. GB1719334.3, dated Nov. 30, 2017, in 9 pages.
Great Britain examination report dated May 30, 2018 in patent application No. GB1719334.3, 4 pp.
Great Britain examination report dated Jul. 20, 2018 in patent application No. GB1719334.3, 3 pp.
Great Britain combined search and examination report dated May 11, 2018 in patent application No. GB1805606.9. 7 pp.
Great Britain examination report dated Jul. 5, 2018 in patent application No. GB1805606.9, 3 pp.
Great Britain examination report dated May 11, 2018 in patent application No. GB1803255.7, 7 pp.
Great Britain examination report dated May 11, 2018 in patent application No. GB1805605.1, 7 pp.
Great Britain examination report in patent application No. GB1501499.6, dated Jun. 1, 2017, in 8 pages.
Great Britain Combined Search and Examination Report under Section 18(3), Application No. GB1501499.6, dated Oct. 12, 2017, in 4 pages.
Indian Examination Report dated Mar. 14, 2019 in patent application No. 1431/KOLNP/2012.
Indian Examination Report dated Mar. 14, 2019 in patent application No. 8767/CHENP/2011.
International Search Report for application No. PCT/NZ2005/000062 dated May 27, 2005.
International Search Report for International application No. PCT/NZ2007/000185, dated Oct. 31, 2007, in 3 pages.
International Search Report, PCT/NZ2009/000072, dated Jul. 28, 2009, 4 pages.
International Search Report, International application No. PCT/NZ2009/000219, dated Feb. 2, 2010, 3 pages.
International Preliminary Report on Patentability (IPRP), International application No. PCT/NZ2009/000219, dated Apr. 12, 2011, 9 pages.
International Search Report, PCT/NZ2010/000229, dated Mar. 18, 2011, 8 pages.
International Preliminary Report on Patentability and Written Opinion of the ISA, International application No. PCT/NZ2010/000229, dated May 22, 2012, 14 pages.
International Search Report, PCT/NZ2011/000211, dated Feb. 17, 2012, 4 pages.
Written Opinion, PCT/NZ2011/000211, dated Feb. 17, 2012, 7 pages.
International Search Report, application No. PCT/NZ2013/000138, dated Nov. 1, 2013, 7 pages.
Written Opinion of the International Searching Authority, PCT/NZ2013/000139, dated Nov. 1, 2013.
International Search Report for International application No. PCT/NZ2014/000021, filed Feb. 21, 2014.
Indian Office Action in Patent Application No. 5250/KOLNP/2008, dated May 23, 2017, 8 pages.
Japanese Examination Report in patent application No. 2012-510418, dated Feb. 10, 2014, 4 pages.
Japanese Examination Report in patent application No. 2012-538784, dated Aug. 25, 2014, 3 pages.
Japanese Examination Report in patent application No. 2012-538784, dated Aug. 5, 2015, 8 pages.
Japanese Examination Report in patent application No. 2012-538784, dated Jul. 25, 2016, 2 pages.
Japanese Examination Report in patent application No. 2015-098324, dated Jul. 22, 2015, 8 pages.
Japanese Examination Report in patent application No. 2017-040092, dated Feb. 5, 2018.
Japanese Official Action dated Sep. 3, 2018 in patent application No. 2017-238259.
Japanese examination report in patent application No. 2015-526496, dated Apr. 17, 2017, in 13 pages.
Japanese Examination Report in patent application No. 2015-526496, dated Feb. 28, 2018, 2 pp.
Japanese Decision for Final Rejection dated Jul. 1, 2019 in patent application No. 2017-238259, 2 pp.
U.S. Appl. No. 61/064,406, 34 pages, copy provided by USPTO on Feb. 23, 2009.
U.S. Appl. No. 61/071,893, 43 pages, copy provided by USPTO on Feb. 23, 2009.
U.S. Appl. No. 61/136,617, 82 pages, copy provided by USPTO on Feb. 23, 2009.
Petition for Inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016.
Declaration of Dr. John Izuchukwu, Ph.D., P.E., U.S. Pat. No. 8,479,741, IPR Nos. 2016-1714 & 2016-1718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for Inter Partes Review of U.S. Pat. No. 8,443,807, IPR2016-01726, filed Dec. 13, 2016.
Decision Denying Institution of Inter Partes Review of U.S. Pat. No. 8,443,807 Pursuant to 37 C.F.R. § 42.108, IPR2016-01726, entered Mar. 6, 2017.
Petition for Inter Partes Review of U.S. Pat. No. 8,443,807 Pursuant to 35 U.S.C. §§ 311-19, 37 C.F.R. § 42, IPR2016-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al, published Oct. 1, 2009.
File History of U.S. Pat. No. 8,443,807 to McAuley et al, published Jan. 7, 2010.
Patent Owner's Complaint for *Fisher & Paykel Healthcare Ltd.* v. *ResMed Corp.*, Case No. 2:16-cv-06099-R-AJW (C.D. Cal.), dated Aug. 15, 2016.

(56) References Cited

OTHER PUBLICATIONS

Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.), dated Aug. 16, 2016.
Patent Owner's Complaint for *Fisher & Paykel Healthcare Ltd.* v. *ResMed Corp.*, Case No. 3:16-cv-02068-GPC-WVG (S.D. Cal.), dated Aug. 16, 2016.
Petitioners' Complaint for *ResMed Inc., et al.* v. *Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.) , dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of *Fisher and Paykel Healthcare Limited* v. *ResMed Limited* filed in the Federal Court of Australia.
Second Affidavit of Alistair Edwin McAuley, Dec. 21, 2016, in the matter of *Fisher and Paykel Healthcare Limited* v. *ResMed Limited* filed in the Federal Court of Australia.
Third Affidavit of Alistair Edwin McAuley, Jan. 31, 2017, in the matter of *Fisher and Paykel Healthcare Limited* v. *ResMed Limited* filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.

McGraw-Hill Dictionary of Scientific and Technical Terms, Sixth Edition, 2003, Tube, p. 2200.
Claim Chart for AirFit P10, U.S. Pat. No. 9,333,315, dated Nov. 7, 2018, 3 pp.
Canadian Examination Report in patent application No. 3010066, dated Dec. 19, 2019, 4 pages.
Chinese Fourth Office Action in patent application No. 201610116121.1, dated Sep. 30, 2019, 12 pages.
Chinese First Office Action in patent application No. 201710824612.6, dated Sep. 30, 2019 , 25 pp.
European examination report dated Sep. 5, 2019 in patent application No. 18163847.9, 5 pp.
Scheduling Order dated Jul. 16, 2019 in IPR2019-00180, 12 pp.
Decision to Institute dated Jul. 16, 2019 in IPR2019-00180, 34 pp.
Decision Denying Institute of Inter Partes Review dated Jul. 16, 2019 in IRP2019-00179, 32 pp.
Australian examination report in patent application No. 2018236891, dated Jun. 9, 2020, 3 pages.
Canadian Examination Report in patent application No. 3017161, dated Apr. 22, 2020, 4 pp.
Chinese Second Office Action in patent application No. 201710824612.6, dated May 25, 2020.
European examination report dated Jun. 16, 2020 in patent application No. 18163847.9, 5 pp.
Australian Examination Report No. 2 for patent application No. 2018217307, dated Mar. 3, 2020, 4 pp.
Canadian Examination Report for patent application No. 2880749, dated Feb. 28, 2020, 4 pp.
Chinese Third Examination Report in patent application No. 201610114706.X, dated Jan. 16, 2020, with translation.
European Search Report and Written Opinion dated May 12, 2016 in patent application No. 09746823.5; 11 pages.
European Examination Report, European Application 13828380.9, dated Mar. 3, 2020, 8 pp.
European Examination Report dated Mar. 16, 2020 in patent application No. 18195537.8.
European Search Report in patent application No. 191976761.1, dated Mar. 3, 2020, 10 pages.
Japanese office action dated Sep. 1, 2019 in patent application No. 2018-188040.
Japanese Pretrial Examination Report dated Jan. 7, 2020 in patent application No. 2017-238259.

\* cited by examiner

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND

Field

The present invention relates to apparatus for treating sleep apnea. More specifically, the present invention provides a nasal positive airway pressure device.

Description of Related Art

Obstructive Sleep Apnea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The procedure for administering CPAP treatment has been well documented in both the technical and patent literature. Briefly stated, CPAP treatment acts as a pneumatic splint of the airway by the provision of a positive pressure, usually in the range 4 to 20 cm H·sub·2O. The air is supplied to the airway by a motor driven blower whose outlet passes via an air delivery hose to a nose (or nose and/or mouth) mask sealingly engaged to a patient's face by means of a harness or other headgear. An exhaust port is provided in the delivery tube proximate to the mask. More sophisticated forms of positive airway pressure devices, such as bi-level devices and auto-titrating devices, are described in U.S. Pat. No. 5,148,802 of Respironics, Inc. and U.S. Pat. No. 5,245, 995 of Rescare Limited, respectively.

U.S. Pat. No. 5,477,852 of Airways Ltd, Inc. discloses a nasal positive airway pressure device that has a pair of nasal members each having a cannula tip to be inserted into the nares of the patient. Each cannula is tapered from a substantially circular cross-section outside the patient's nostril to a substantially oval cross-section at the tip inserted into the nostril. An inflatable cuff surrounds each cannula with the interior space of the cuff communicating with the lumen of the cannula through at least one aperture in the sidewall of the cannula. The nasal members are connected to one or more flexible hoses that, in turn, are connected to a source of positive air pressure. In use, positive air pressure is supplied to each cannula tip through the air hoses and nasal members. The positive air pressure inflates the cuffs to hold the nasal members in place and to effect treatment. The nasal device of U.S. Pat. No. 5,477,852 is attached to headgear that is located about a patient's head; this headgear could be considered by many patients as cumbersome and uncomfortable.

Conventional nasal masks used for administrating CPAP treatment are also considered uncomfortable and cumbersome, and prior art nasal masks and the like are noisy (due to air leaks). These disadvantages in many cases are a formidable obstacle to patient acceptance of such treatment. Therefore, a substantial number of patients either cannot tolerate treatment or choose to forego treatment. It is believed a substantial number of such patients could benefit from a nasal positive airway pressure apparatus that is more convenient to use and comfortable to wear, thereby resulting in increased treatment compliance.

As oxygen is supplied as a dry gas it is well known in the art to either heat and/or humidify gases before delivering them for breathing by a patient. In particular when delivering oxygen, or oxygen or air mixture, it has proven beneficial to humidify the gases first. In WO01/41854 of Vapotherm, Inc. a system is disclosed that allows the delivery of humidified oxygen through a nasal cannula. This system uses a narrow bore conduit and nasal cannula with a high resistance to gas flows, thereby requiring the oxygen be of a high pressure. Air, as well as oxygen can also be passed down the conduit and nasal cannula and it too must be of a high pressure. This system allows the delivery of high flows of oxygen enriched air to the patient, but is limited in the flows achievable due to the narrow bore of the cannula resulting in high resistance gas flow and excessive velocity and noise upon exiting the cannula. Furthermore, the narrowness of the nasal cannula in this system allows easy expiration of gases between the prongs and nares and therefore does not create any positive airway pressure.

Innomed Technologies, Inc. manufactures a nasal cannula device called the NASALAIRE™. In this device air or oxygen travels down a wide bore conduit to nasal cannula. The NASALAIRE™ creates a physical seal between the nares and itself, and relies on the absence of leaks around itself and the nares to deliver pressure supplied by a continuous positive airway pressure (CPAP) blower to the airway of the wearer.

SUMMARY

It is an object of the present invention to provide a breathing assistance apparatus which goes someway to overcoming the above mentioned disadvantages or which will at least provide the public a useful choice.

Accordingly in a first aspect the present invention consists in a breathing assistance apparatus comprising:
  nasal cannula, shaped to fit within a user's nares, and adapted to deliver said humidified gases to said user,
  a pressurised source of gases,
  transportation means adapted to, in use, be in fluid communication with said source of gases and said nasal cannula and adapted to in use convey said gases to said user,
  wherein said nasal cannula including at least one prong allowing high flow delivery of said humidified gases and creating a positive airway pressure in said patient's airway, said at least one prong having an angled end, such that in use, gases flowing through said prong are directed to said user's nasal passages.

In a second aspect the present invention consists in a breathing assistance apparatus comprising:
  nasal cannula, shaped to fit within a user's nares,
  a pressurised source of gases, transportation means adapted to, in use, be in fluid communication with said source of gases and said nasal cannula and adapted to in use convey said gases to said user, wherein said nasal cannula are adapted to deliver said humidified gases to said user, said nasal cannula including at least one prong allowing high flow delivery of said humidified gases and creating positive airway pressure in said patient's airway, said at least one prong having an end that is flared outwardly.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Preferred forms of the present invention will now be described with reference to the accompanying drawings.

DETAILED DESCRIPTION

Whether used in a hospital environment or in a home environment, the nasal cannula of the present invention will generally have associated three main pieces of apparatus. Firstly, an active humidifier, which that controls the temperature of a heater plate heating a body of water to achieve a desired temperature and humidity of the gases being humidified. Secondly, a transport conduit from the humidifier to the patient is also required, which is preferably heated to reduce condensation, or "rain out". Thirdly, a cannula designed to fit into the nasal cavity and deliver humidified, pressurized gases. In particular, in one embodiment the nasal cannula of the present invention has two flared end prongs that seal within a patient's nares, although in some embodiments the cannula may have a single prong. The cannula prongs are shaped such that a step is created between them so that the prongs abut the user's nasal septum in use. Furthermore, the gripping action of the sides of the prongs to the user's septum in use prevents the prongs from dislodging from the user's nares. In another embodiment the prongs of the nasal cannula are angled toward one another as well as having an angled profile at the outlet of gases, such that gases flow from the prongs flows back into the nasal passage and is not forced up into the rest of the nasal cavity.

Figure 1:
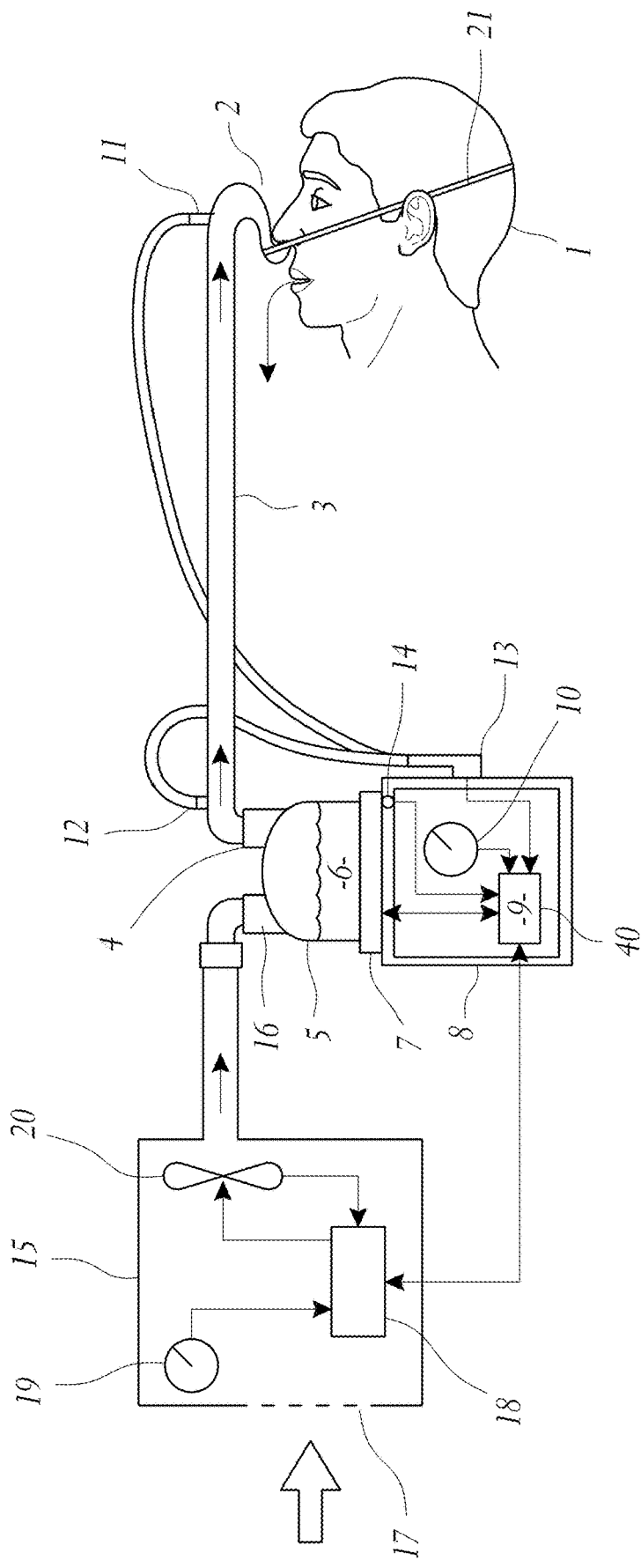
FIG. 1 is a block diagram of a system providing humidified continuous positive airway pressure to a user as might be used in conjunction with a nasal cannula of the present invention.

With reference to FIG. 1 a humidified Continuous Positive Airway Pressure (CPAP) system is shown in which a patient 1 is receiving humidified and pressurised gases through the nasal cannula 2 of the present invention. The cannula 2 is connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 that contains a volume of water 6. The inspiratory conduit 3 may contain heating means or heater wires (not shown) which heat the walls of the conduit to reduce condensation of humidified gases within the conduit. The humidification chamber 6 is preferably formed from a plastics material and may have a highly heat conductive base (for example an aluminium base) which is in direct contact with a heater plate 7 of humidifier 8. The humidifier 8 is provided with control means or electronic controller 9 that may comprise a microprocessor based controller executing computer software commands stored in associated memory.

The controller 9 receives input from sources such as user input means or dial 10 through which a user of the device may, for example, set a predetermined required value (preset value) of humidity or temperature of the gases supplied to patient 1. The controller may also receive input from other sources; for example, temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. A flow of gases (for example air) is provided to the chamber through inlet 16 from a gases supply means or blower 15. As the volume of water 6 within humidification chamber 5 is heated, water vapour begins to fill the volume of the chamber above the water's surface and is passed out of the humidification chamber 5 through outlet 4. Exhaled gases from the patient's mouth are passed directly to ambient surroundings in FIG. 1.

The blower 15 is provided with variable pressure regulating means or a variable speed fan 20 which draws air or other gases through the blower inlet 17. The speed of the variable speed fan 20 is controlled by the electronic controller 18 (or alternatively the function of the controller 18 could carried out by the controller 9) in response to inputs from the controller 9 and a user set predetermined required value (preset value) of pressure or fan speed via the dial 19.

Flared Prong Nasal Cannula

Figure 2:
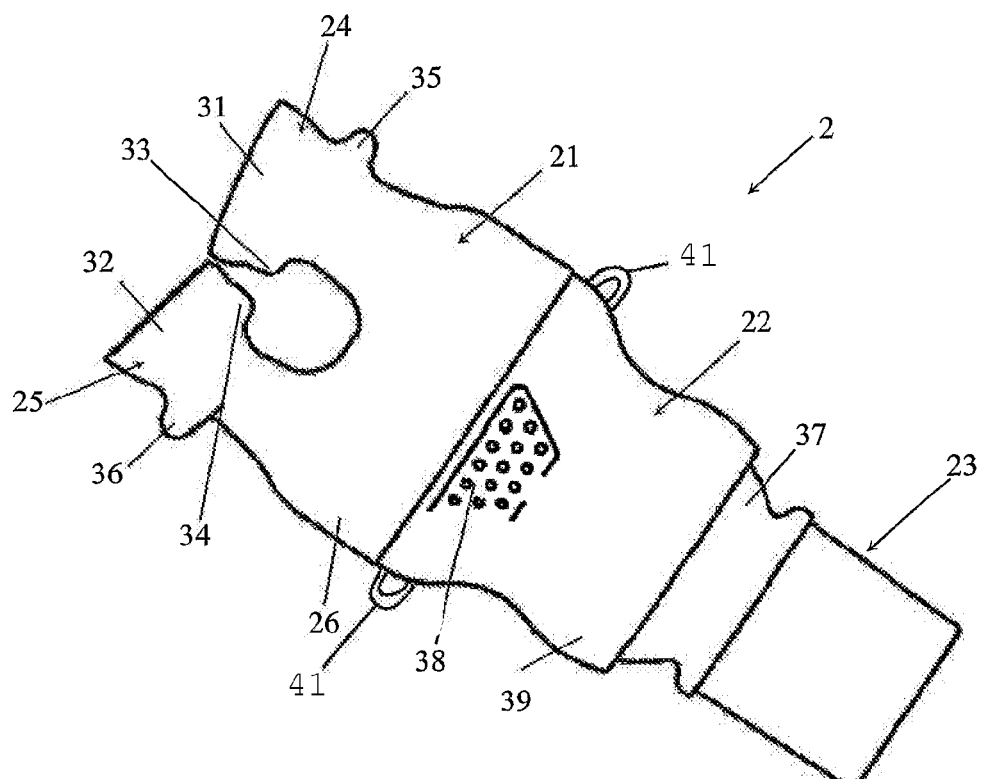
FIG. 2 is a perspective view of a first embodiment of the nasal cannula of the present invention.
Figure 3:
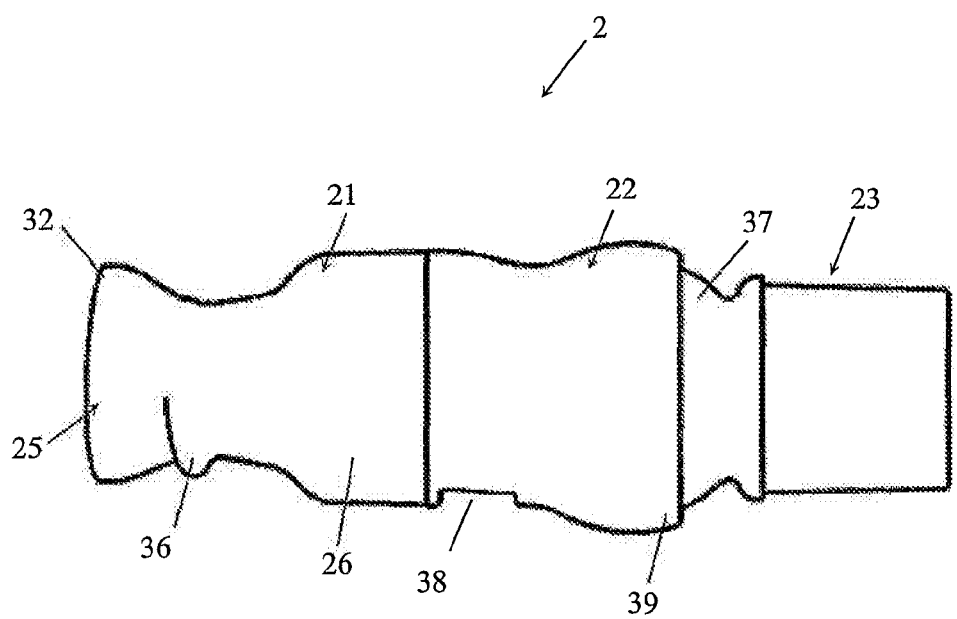
FIG. 3 is a side view of the nasal cannula of FIG. 2.
Figure 4:
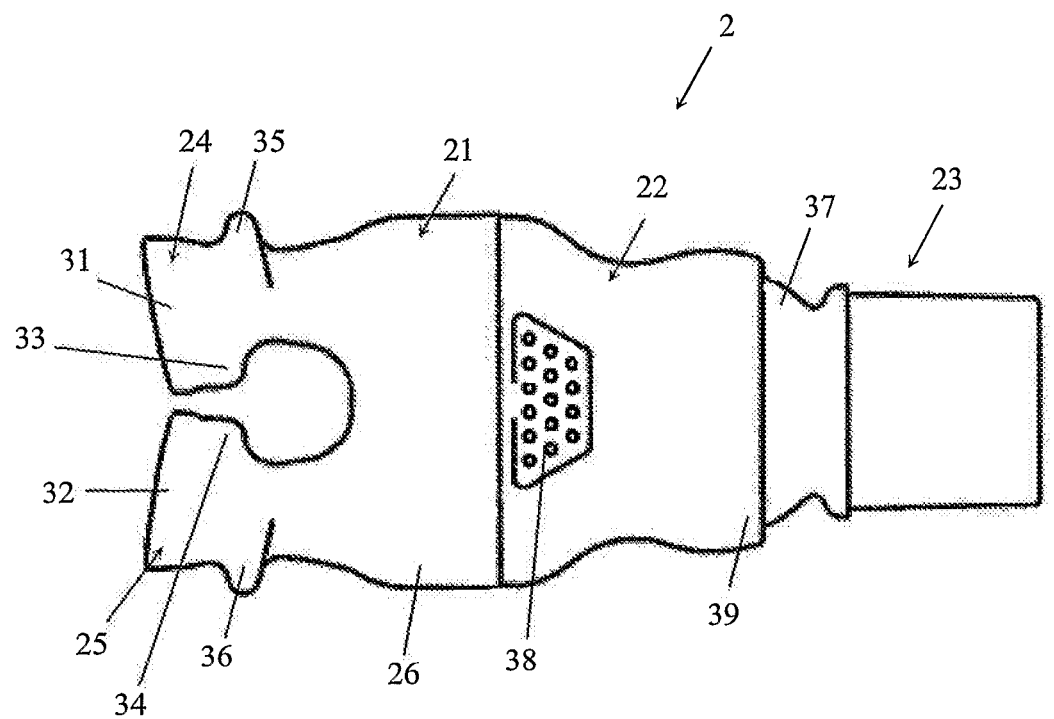
FIG. 4 is a plan view of the nasal cannula of FIG. 2.
Figure 5:
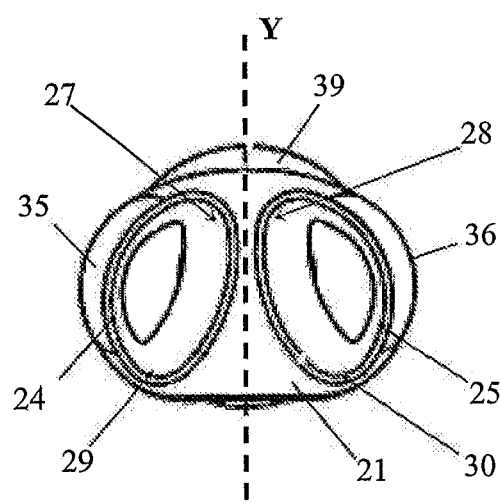
FIG. 5 is a prong end view of the nasal cannula of FIG. 2
Figure 6:
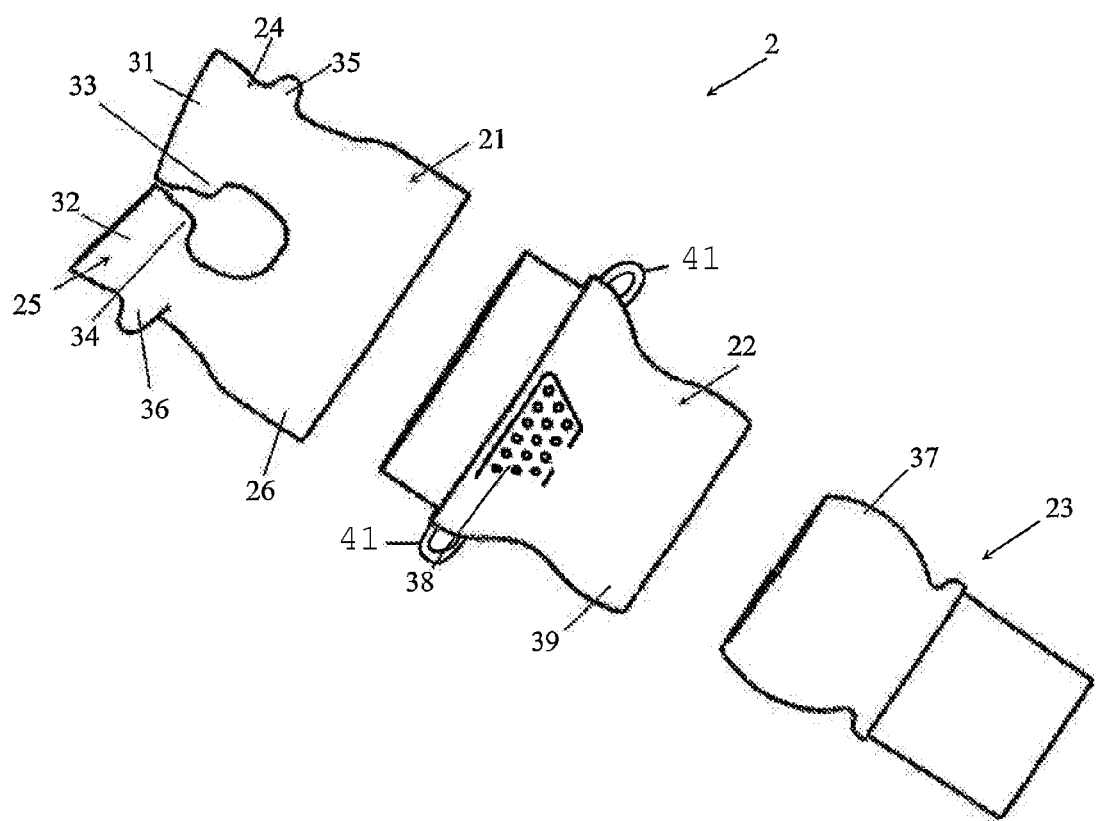
FIG. 6 is an exploded view of the nasal cannula of FIG. 2.

A first embodiment of a nasal cannula of the present invention is shown in detail in FIGS. 2 to 6. Referring to FIGS. 2 and 6, the nasal cannula 2 comprises three main components; the prong part 21, body part 22 and ball connector 23.

The prong part 21 has two nasal prongs 24, 25, each of which are substantially shaped to follow the contours of the human nares and in use are placed inside a user's nares. The prongs 24, 25 extend out from a hollow tubular body 26 that in use fits to the body part 22. Each of the prongs 24, 25 are integrally moulded with the tubular body 26 in a flexible plastics material or rubber, such as silicone, other thermoset elastomers or thermoplastic elastomers such as Kraton™. The prongs 24, 25 are substantially oval tubular members that allow for a passage of gases. In particular, as shown in FIG. 5, the prongs are oval in shape and angled in the same manner as a human's nares. The prongs 24, 25 are angled toward one another (or toward the vertical axis Y) at the top 27, 28 of the prongs and away from one another at the bottom 29, 30 of the prongs. Furthermore, the ends 31, 32 of the prongs flare outwardly and preferably are formed such that the ends of the prongs are thinner in cross-section than the rest of the prongs. The flared thinner section ends 31, 32 of the prongs assist with the sealing of the prongs 24, 25 in use within the user's nares. When in use and with gases flowing through the prongs the force of the gas pressure will force the prong ends 31, 32 to flare outwardly and seal against the inside of the user's nares.

The prongs 24, 25 each include a step 33, 34 formed along their lengths. Each of the steps 33, 34 are formed on the prongs 24, 25 in an opposing manner such that in use, when the prongs are within a user's nares the steps 33, 34 abut the user's nasal septum and form a ledge that prevents dislodgement of the prongs. The prongs 24, 25 also have protrusions 35, 36 formed on their outer edges that abut the sides of the user's nares (opposite to the nasal septum). The protrusions 35, 36 assist in preventing the dislodgement of the prongs, especially if the user moves his or her head. The protrusions 35, 36 also maintain the prongs within the user's nares in a correct orientation such that in use gases flow through the prongs and directly up the user's nasal passages.

The body part 22 is a tubular passageway in which the prong part 21 is connected at one end and a ball joint 37 at the other end. The ball joint 37 extends from the connector 23 and slots into a complementary shaped (partial sphere) socket end 39. The body part 22 also has a number of apertures 38 formed in it, which act as a bias flow outlet vent. Therefore, any gases exhaled by the user through their nose will exit through the apertures 38.

The connector 23 is preferably connected to the inspiratory conduit 3 (see FIG. 1) that supplies gases flow to the cannula 2. The inspiratory conduit 3 may be moulded directly to the connector 23 or other connection mechanisms may be used, such as a friction fit formed between the connector and conduit.

Although a ball and socket joint, as described above, between the body part 22 and connector 23 is preferred other connections may be utilised, such as a flexible piece of silicone, or other appropriate connection. The connection between the cannula body and connector must be able to be flexed or rotated to allow for the inspiratory conduit 3 to be moved without causing the dislodgement of the nasal cannula 2 from the user's nares.

In the preferred form of the nasal cannula 2 of the present invention the body part 22 and connector 23 are preferably made from a hard or rigid plastics material, such as polypropylene, polycarbonate or acetyl. In other forms the body part 22 and connector 23 may be of different plastics materials to allow for increased slidability between these parts.

The prong part 21 may be supplied in various different sizes such that different sized user's may remove an existing prong part and simply attach a different sized flexible plastics prong part over the body part 22.

To provide additional comfort for the user or ensure the nasal cannula of the present invention do not fall from a user's nares, the nasal cannula may be used in combination with a headgear strap, which in one embodiment is a small flexible tube. For example, FIG. 1 shows a headgear strap 40 extending from the nasal cannula 2. The ends of the headgear strap that attach to the cannula may attach to extensions (or loops) 41 on the body part 22 of the cannula shown in FIG. 2, or may attach about other appropriate areas of the cannula, for example, about the connector 23.

The abovementioned embodiment of the nasal cannula 2 of the present invention is preferably a wide bore pronged cannula used for high flow conditions.

Figure 7:
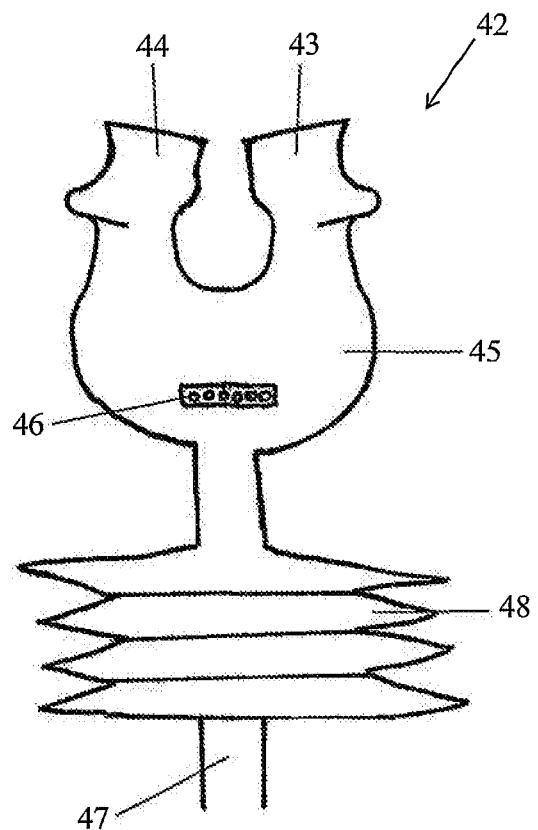
FIG. 7 is a side view of a second embodiment of a nasal cannula of the present invention.

A second embodiment of the present invention is shown in FIG. 7. In this embodiment of the nasal cannula 42 the prongs 43, 44 are preferably small bore prongs for use with lower flow conditions. The prongs 43, 44 are similarly shaped to the prongs 24, 25 detailed above, but may not seal in the same manner as the abovementioned prongs due to the smaller size of the prongs. In fact these prongs may not seal at all in use within the user's nares.

Furthermore, in this second embodiment the nasal cannula 42 is smaller and weighs less as it is only comprised of a prong body 45 and prongs 43, 44, where the body 45 is connected to a small tube that is formed with corrugations or bellows 48 that connect to an inspiratory tube or conduit 47 (similar to the inspiratory conduit 3 described above) that receives a supply of gases.

The corrugations of bellows 48 will bend or move when a weight or force is placed on the cannula, thereby preventing dislodgement of the cannula 42 from a user's face in use. In particular, the corrugations or bellows 48 prevent transferral of the torque onto the cannula 42 when a user moves his or her head.

The body 45 of the cannula 42 is provided with a number of apertures 46 that allows for gases exhaled by the users to be expelled into the ambient air.

The prong body and prongs of this embodiment of the cannula of the present invention are preferably formed a flexible plastics material or rubber, such as silicone, other thermoset elastomers or thermoplastic elastomers such as Kraton™.

Figure 8:
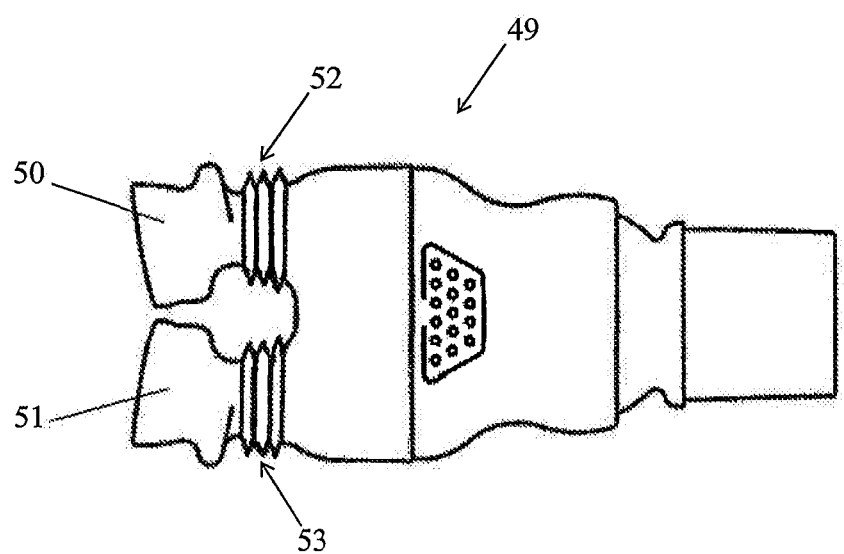
FIG. 8 is a side view of a third embodiment of a nasal cannula of the present invention.
Figure 9:
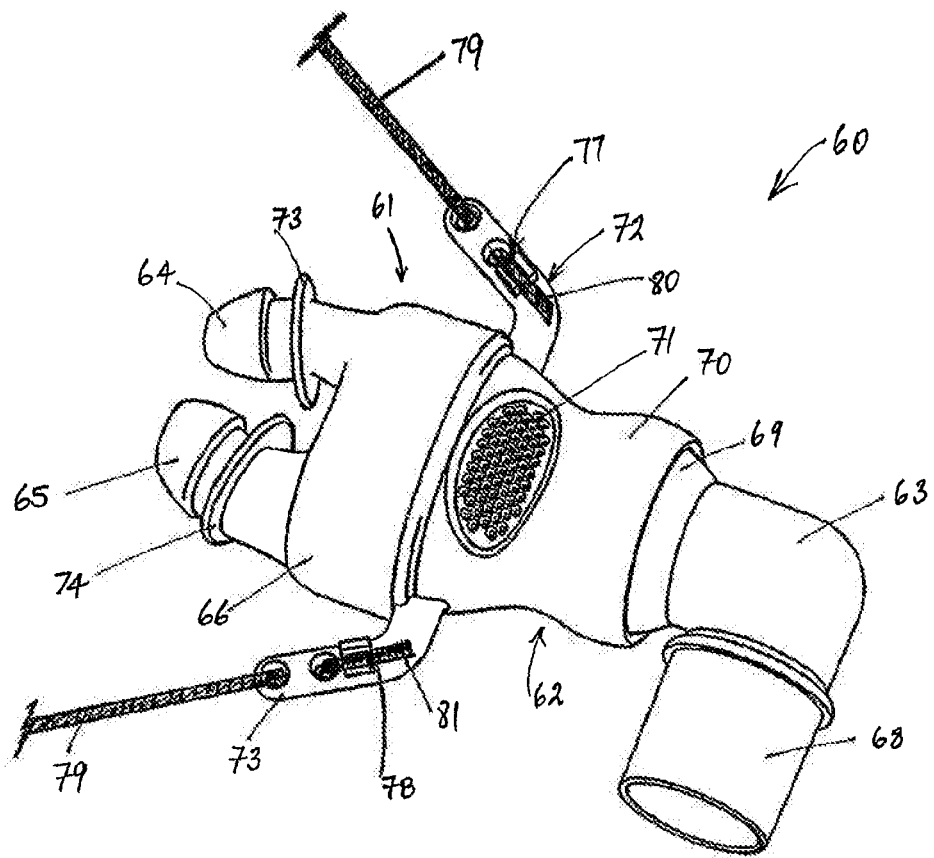
FIG. 9 is a perspective view of a fourth embodiment of a nasal cannula of the present invention.

A third embodiment of the nasal cannula of the present invention is shown in FIG. 8 where the cannula may be provided with corrugated or baffled sections on the prongs. The nasal cannula 49 of this embodiment is similar to that of FIG. 2 but the prongs 50, 51 have a series of corrugations 52, 53 formed in them. The corrugations 52, 53 allow for movement of each of the prongs 50, 51 for a better user fit, and allow for movement of the cannula 49 without causing dislodgement of the prongs from the user's nares.

Angled Prong Nasal Cannula

A fourth embodiment of the nasal cannula of the present invention is shown in FIGS. 9 to 13. The nasal cannula 60 has a similar construction to the nasal cannula of FIG. 2 and comprises three main components; a prong part 61, body part 62 and ball jointed connector 63.

The prong part 61 preferably has two nasal prongs 64, 65, each of which are substantially shaped to follow the contours of the human nares and in use are placed inside a user's nares. In some forms a cannula with only one prong may be provided. The prongs 64, 65 extend out from a hollow tubular body 66 that in use fits to the body part 62, preferably about an extension 67 (as shown in the exploded view of the nasal cannula of FIG. 11). Each of the prongs 64, 65 are integrally moulded with the tubular body 66 in a flexible plastics material or rubber, such as silicone, other thermoset elastomers or thermoplastic elastomers, such as Kraton™. The prongs 64, 65 are substantially oval tubular members that allow for a passage of gases.

Figure 12:
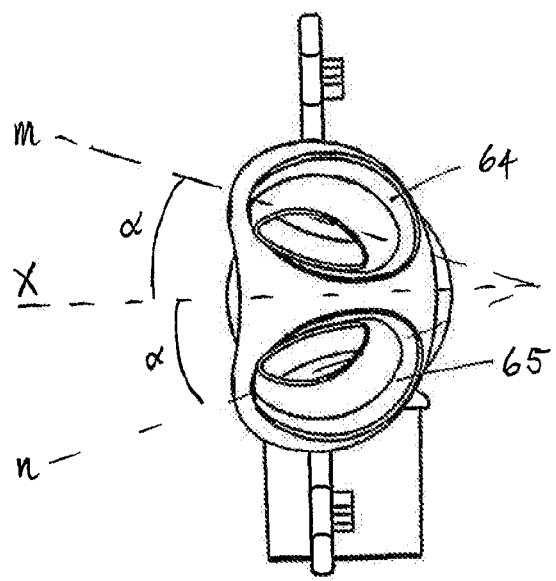
FIG. 12 is a front view of the prongs of the nasal cannula of FIG. 9.
Figure 13:
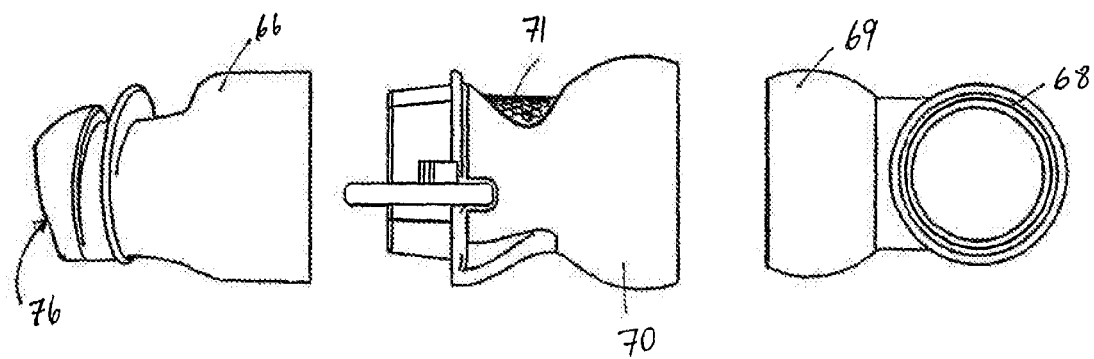
FIG. 13 is an exploded side view of the nasal cannula of FIG. 9.

In particular, as shown in FIG. 12, the prongs are oval in shape (to reflect the shape of human nares) and angled in the same manner as a human's nares. The prongs 64, 65 are angled toward one another (or toward the horizontal axis X) such that angles a are formed between the midlines m, n through each respective prong 64, 65. The angled profile of the prongs 64, 65 means that they are more ergonomically correct with a human's nares and may assist in directing the gases flow from the prongs to the user's nasal cavities. The prongs 64, 65 are constructed such that their cross-sectional width narrows closer to the tip of each prong.

Figure 10:
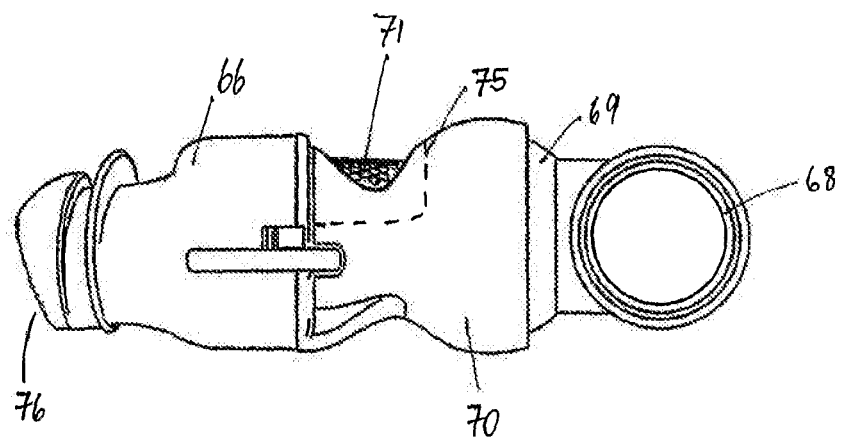
FIG. 10 is a side view of the nasal cannula of FIG. 9.
Figure 11:
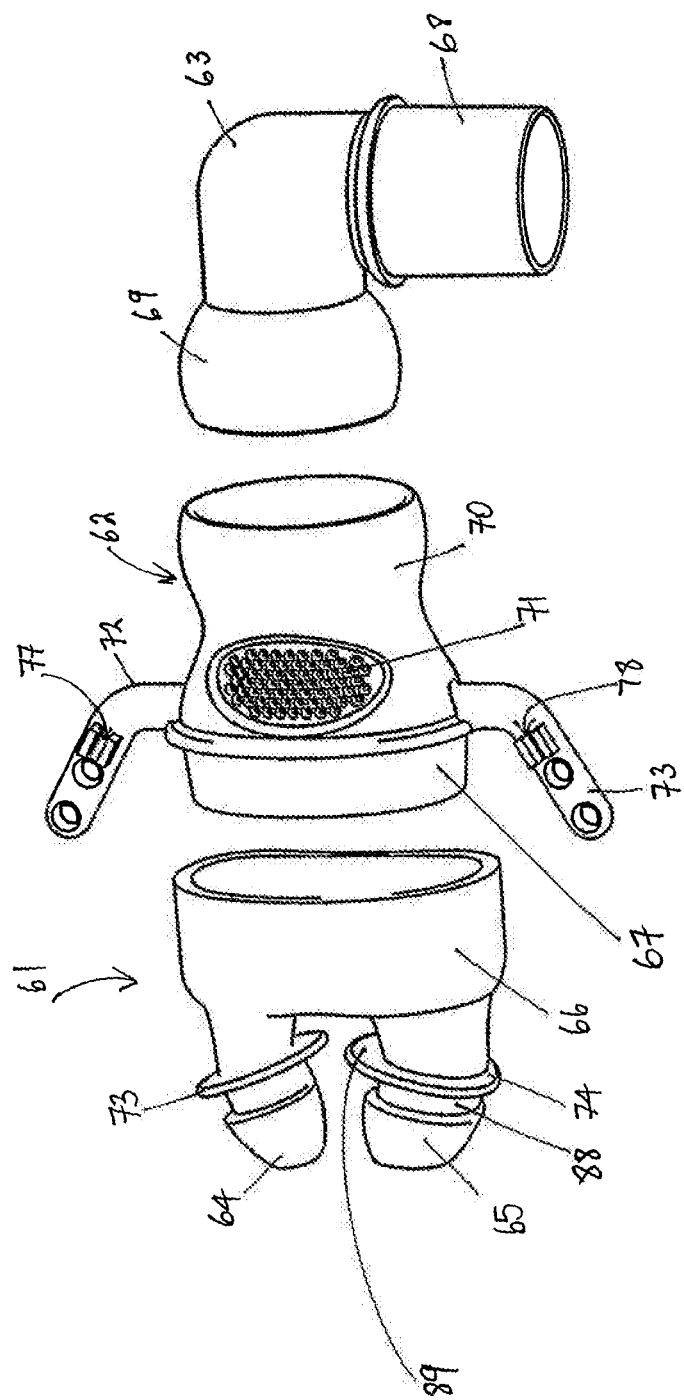
FIG. 11 is an exploded perspective view of the nasal cannula of FIG. 9.

In the preferred form the prongs 64, 65 have an angled and profiled end 76 (see FIG. 10). The angled ends 76 assist in directing gases flow to the user's nasal passages.

Each of the prongs 64, 65 has a flange 73, 74 disposed about its circumference. The flanges 73, 74 are at a position on the prongs 64, 65 such that the each of the flanges rests against the outside of each of the patient's nares. The flanges 73, 74 do not extend inside the nares, but rest at the entranceway of the user's nares, and preferably seal the nares. In some users the flanges 73, 74 may extend within the user's nares and provide sealing of the nares. The flanges 73, 74 are preferably thin flexible extensions that extend substantially completely around the circumference of the prongs 64, 65. The flanges 73, 74 are preferably substantially elliptical in shape with one side (for example, side 89, which in use will abut the nasal septum of a user) of the flange extending out from each prong further than the other side of each prong. There is a recessed area 88 on each of the prongs between the flange and the shaped ends of the prongs in which preferably in use the ends of a user's nares rest.

The body part 62 is a tubular passageway in which the prong part 61 is connected at one end and a ball joint 69 at the other end. The ball joint 69 extends from the connector 63 and slots into a complementary shaped (partial sphere) socket end 70 on the body part 62. The body part 62 may also have a plurality of apertures 71 formed in it, which acts as a bias flow outlet vent. Therefore, any gases exhaled by the user through their nose will exit through the apertures 71.

A shield 75 (illustrated by the dashed line in FIG. 10) may extend over the bias vent 71 inside the body part 70 to prevent gases from the blower (gases supply 15) from interacting with the bias vent 71 and vent holes, causing noise in use.

Figure 16:
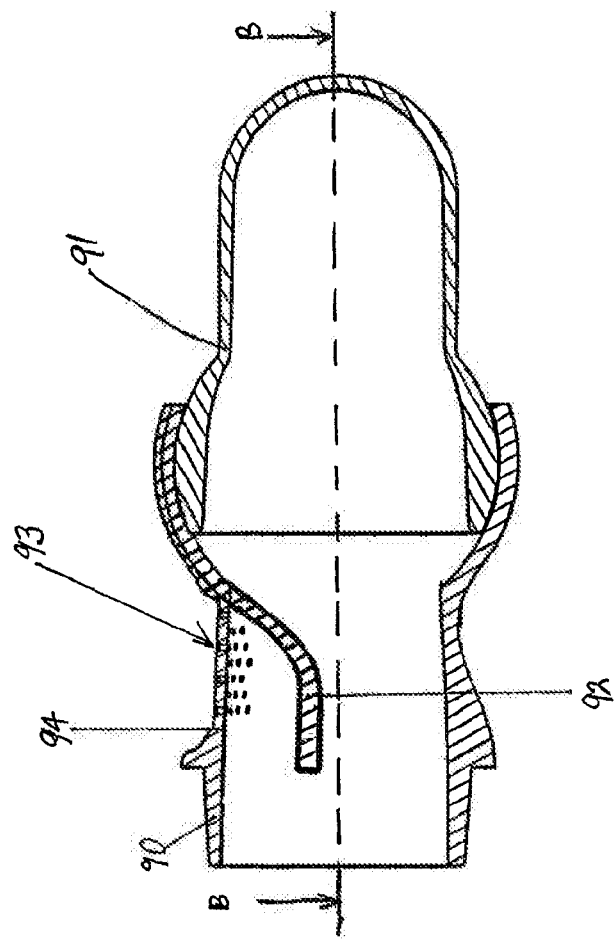
FIG. 16 is a side cross-sectional view of a sixth embodiment of the nasal cannula of the present invention including a shield that protects an outlet vent from inlet gases.
Figure 17:
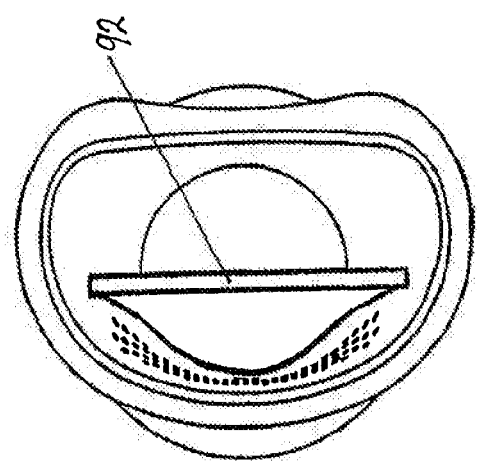
FIG. 17 is a cross-section through BB of the nasal cannula of FIG. 16.

In a sixth embodiment as shown in FIGS. 16 and 17 a nasal cannula without a prong part is shown, but that includes a shield similar to that described above. In this embodiment a body part 90 and a ball jointed connector 91 fit together as described above. The body part 90 includes an expiratory vent shield 92 that extends down from the top wall 94 of the body part 90 and shields the outlet vent 93.

Referring back to FIGS. 10 to 13, preferably the ball joint connector 63 is angled and extends into a swivelable connector 68. The swivel connector 68 is capable in use of being connected to the inspiratory conduit 3 (see FIG. 1) that supplies gases flow to the cannula 60. The inspiratory conduit 3 may be moulded directly to the connector 68 or other connection mechanisms may be used, such as a friction fit formed between the connector 68 and the conduit 3.

In other forms of the present invention the ball joint connector 63 or the ball joint 69 may have formed in it a plurality of channels. One example of this is the embodiment of FIGS. 14 and 15. Such channels allow there to be a leak when gases flow through the connector to the cannula and prongs. The channels are therefore capable of acting as a bias flow and a separate bias flow out outlet (such as that outlet 71 described above) may not be required.

Figure 14:
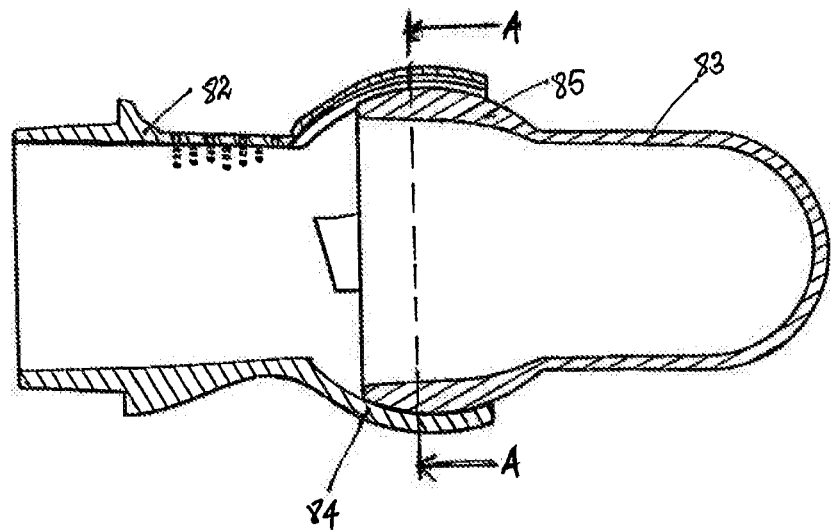
FIG. 14 is a side cross-sectional view of a fifth embodiment of the nasal cannula of the present invention where the connection between a body part and connector of the cannula includes a plurality of channels.
Figure 15:
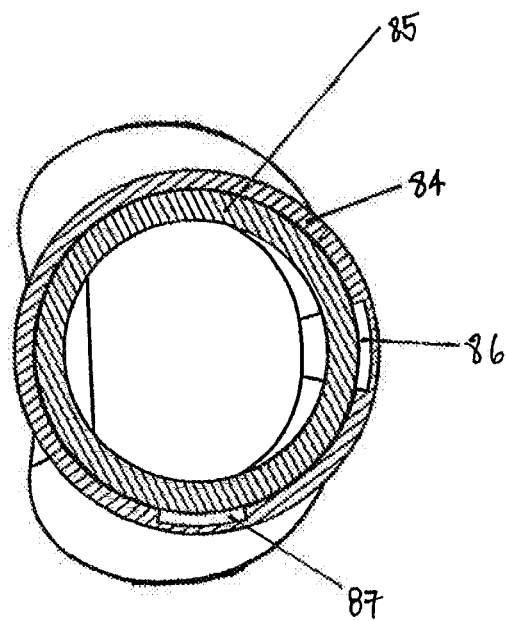
FIG. 15 is a cross-section through AA of the nasal cannula of FIG. 14.

In FIGS. 14 and 15 only a body part 82 and ball jointed connector 83 are shown. The body part 82 and ball jointed connector 83 join in a manner as described above, where the substantially half sphere shaped end 84 of the body part 82 receives the substantially half sphere shaped end 85 of the connector 83. The ends 84, 85 enable a rotation between the body part 82 and connector 83. In this embodiment two channels 86, 87 are formed in the connector end 85. Two channels are shown in this embodiment but there may be only one or any number of channels. Similarly, channels may be formed in the body part end 84.

It is preferred that there is a ball and socket joint, as described above, between the body part 62 and connector 63, although other connections may be utilised, such as a flexible piece of silicone, or other appropriate connection. The connection between the cannula body and connector must be able to be flexed or rotated to allow for the inspiratory conduit 3 to be moved without causing the dislodgement of the nasal cannula 60 from the user's nares.

In the preferred form of the nasal cannula 60 of the present invention the body part 62, connector 63, ball joint 69 and swivel connector 68 are preferably made from a hard or rigid plastics material, such as polypropylene, polycarbonate or acetyl. In other forms these may be of different plastics materials to allow for increased slidability between these parts.

The prong part 61 may be supplied in various different sizes such that different sized user's may remove an existing prong part and simply attach a different sized flexible plastics prong part over the body part 62.

To provide additional comfort for the user or ensure the nasal cannula of the present invention does not fall from a user's nares, the nasal cannula 60 is preferably used in combination with a headgear strap. The strap may be similar to that shown in FIG. 1 with relation to the first form of the nasal cannula 2. In this fourth form of the nasal cannula 60 the body part 62 has headgear extensions 72, 73 that extend out from the body part 70. The extensions 72, 73 each have a channel 77, 78 formed in them that is capable of receiving an end 80, 81 of the headgear strap 79. The strap ends 80, 81 in use are threaded through apertures (preferably two) and extend into and are held in the channels 77, 78. In this form the headgear strap 79 is made from a small diameter silicon, rubber or similar type material. Therefore, when the strap ends 80, 81 are threaded through the apertures friction is created that maintains the straps within the apertures and prevents the straps from slipping from the cannula.

In other forms the ends of the headgear strap that attach to the cannula may attach to extensions (or loops) 41 on the body part 22 of the cannula shown in FIG. 6, or may attach about other appropriate areas of the cannula, for example, about the connector 23.

What is claimed is:

1. A mask assembly for delivering positive airway pressure to a user in use, the mask assembly comprising:
   a seal member comprising a distal end with a first opening and a proximal end with at least a second opening, the first opening configured to receive pressurized gases, and the proximal end configured to seal against a user in use and provide the pressurized gases to the user;
   a body part comprising a connector end, a seal member end in fluid communication with the first opening of the seal member, and an inspiratory gas passage with an inspiratory gas inlet and an inspiratory gas outlet, the inspiratory gas inlet comprising an inner partially spherical socket disposed at the connector end of the body part, the inspiratory gas outlet having a height and a width, the width being greater than the height; and
   an angled connector comprising a partially spherical end in fluid communication with a swivelable end, wherein the partially spherical end slots into the connector end of the body part and allows rotation between the angled connector and the body part, and wherein the swivelable end is configured to connect to an inspiratory conduit configured to deliver a pressurized flow of gases into the partially spherical connector.

2. The mask assembly of claim 1, wherein the connector end comprises a round opening to the inner partially spherical socket.

3. The mask assembly of claim 1, wherein the seal member end comprises at least one circumferential extension connected to the first opening of the seal member.

4. The mask assembly of claim 1, wherein the angled connector defines a connector gas passage extending between the partially spherical end and the swivelable end.

5. The mask assembly of claim 1, wherein the partially spherical end slots into the inner partially spherical socket of the body part forming a ball jointed connection.

6. The mask assembly of claim 1, wherein the inner partially spherical socket comprises a first diameter, and wherein the height of the inspiratory gas outlet is less than the first diameter.

7. The mask assembly of claim 1, wherein the inspiratory gas outlet comprises an upper edge, a lower edge, and a height defined by a first distance between the upper and lower edges, the inspiratory gas outlet further comprising a left edge, a right edge and a width defined by a second distance between the left and right edges.

8. The mask assembly of claim 1, the body part further comprising:
   first and second curved lateral sides, the inspiratory gas outlet having a first height at a location between the first and second curved lateral sides;
   a first headgear extension having a distal end, the distal end of the first headgear extension connected to the body part at the first curved lateral side, the distal end of the first headgear extension having a second height smaller than the first height;
   a second headgear extension having a distal end, the distal end of the second headgear extension connected to the second curved lateral side, the distal end of the second headgear extension having a third height smaller than the first height;
   a headgear strap connected to the first and second headgear extensions and configured to support the mask assembly against a user's face in use.

9. The mask assembly of claim 1, wherein the seal member comprises a flexible portion formed of a flexible material, the mask assembly additionally comprising a first headgear extension having a distal end on a distal side of the flexible portion at a location spaced from a user in use, and a proximal end disposed proximally toward a left side of a user's face in use, and a second headgear extension having a distal end on the distal side of the seal member at a location spaced from a user in use, and a proximal end disposed proximally toward a right side of a user's face in use.

10. The mask assembly of claim 9 wherein, the first headgear extension comprises a first portion and a second portion, the first portion of the first headgear extension comprising the distal end of the first headgear extension and extending at least along a first lateral direction extending laterally away from and beyond an outer periphery of the seal member, the second portion of the first headgear extension extending from the first portion, along a second direction extending more proximally toward the user than the first direction in use, the second headgear extension comprising a first portion and a second portion, the first portion of the second headgear extension comprising the distal end of the second headgear extension and extending at least along a third lateral direction extending laterally away from and beyond the outer periphery of the seal member, the second portion of the second headgear extension extending from the first portion, along a fourth direction extending more proximally toward the user than the third direction in use.

11. A mask assembly for delivering positive airway pressure to a user in use, the mask assembly comprising:
    a seal assembly comprising a seal assembly inlet and a seal assembly outlet, the seal assembly inlet configured to receive pressurized gases, and the seal assembly outlet configured to seal against a user in use and provide pressurized gases to the user;
    a body part comprising a distal end and a proximal end, an inspiratory gas passage, an expiratory gas passage, and a gas passage shield disposed between the inspiratory gas passage and the expiratory gas passage, the inspiratory gas passage comprising an inspiratory gas inlet comprising an inner partially spherical socket at the distal end and an inspiratory gas outlet at the proximal end fluidically communicating with the seal assembly inlet, the gas passage shield extending along at least one side of the inspiratory gas outlet, the inspiratory gas outlet having a height and a width, the width being greater than the height; and
    a partially spherical connector comprising a partially spherical end with a connector outlet and a swivelable end with a connector inlet, the partially spherical end comprising a partially spherical outer surface disposed within the inner partially spherical socket, and wherein the swivelable end is configured to connect to an inspiratory conduit configured to deliver pressurized gases into the partially spherical connector.

12. The mask assembly of claim 11 additionally comprising a bias flow outlet vent disposed on the body part configured to vent expiratory gas from the expiratory gas passage to an exterior of the body part.

13. The mask assembly of claim 12, wherein the bias flow outlet vent comprises a plurality of vent holes.

14. The mask assembly of claim 12, wherein a distal end of the gas passage shield is disposed between the bias flow outlet vent and the inner partially spherical socket.

15. The mask assembly of claim 11, wherein the gas passage shield curves inwardly into the inspiratory gas passage.

16. The mask assembly of claim 11, wherein the gas passage shield defines a constriction of the inspiratory gas passage.

17. The mask assembly of claim 11 wherein the distal end of the body part comprises a round opening and the inspiratory gas passage transitions from the round opening to the inspiratory gas outlet.

18. The mask assembly of claim 11, wherein the inner partially spherical socket comprises an inner partially spherical socket surface with a diameter, the height of the inspiratory gas outlet being less than the diameter.

19. The mask assembly of claim 11, wherein the seal assembly comprises a flexible portion formed of a flexible material, the mask assembly additionally comprising a first headgear extension having a distal end on a distal side of the flexible portion at a location spaced from a user in use, and a proximal end disposed proximally toward a left side of a user's face in use, and a second headgear extension having a distal end on the distal side of the prong part at a location spaced from a user in use, and a proximal end disposed proximally toward a right side of a user's face in use.

20. The mask assembly of claim 19 wherein, the first headgear extension comprises a first portion and a second portion, the first portion of the first headgear extension comprising the distal end of the first headgear extension and extending at least along a first lateral direction extending laterally away from and beyond an outer periphery of the seal assembly, the second portion of the first headgear extension extending from the first portion, along a second direction extending more proximally toward the user than the first direction in use, the second headgear extension comprising a first portion and a second portion, the first portion of the second headgear extension comprising the distal end of the second headgear extension and extending at least along a third lateral direction extending laterally away from and beyond the outer periphery of the seal assembly, the second portion of the second headgear extension extending from the first portion, along a fourth direction extending more proximally toward the user than the third direction in use.

* * * * *